(12) United States Patent
Ye et al.

(10) Patent No.: US 12,030,841 B2
(45) Date of Patent: Jul. 9, 2024

(54) HONOKIOL CRYSTAL FORMS, AMORPHOUS FORM AND PREPARATION THEREOF

(71) Applicant: Chengdu Jinrui Foundation Biotech Co., Ltd., Sichuan (CN)

(72) Inventors: Haoyu Ye, Sichuan (CN); Tianmin Zhu, Sichuan (CN); Neng Qiu, Sichuan (CN)

(73) Assignee: Chengdu Jinrui Foundation Biotech Co., Ltd. (CN)

( * ) Notice: Subject to any disclaimer, the term of this patent is extended or adjusted under 35 U.S.C. 154(b) by 610 days.

(21) Appl. No.: 17/277,123

(22) PCT Filed: Jan. 20, 2021

(86) PCT No.: PCT/CN2021/072853
§ 371 (c)(1),
(2) Date: Mar. 17, 2021

(87) PCT Pub. No.: WO2022/141648
PCT Pub. Date: Jul. 7, 2022

(65) Prior Publication Data
US 2022/0204432 A1  Jun. 30, 2022

(30) Foreign Application Priority Data
Dec. 31, 2020 (CN) .......................... 202011620565.1

(51) Int. Cl.
| | |
|---|---|
| C07C 37/84 | (2006.01) |
| A61K 9/127 | (2006.01) |
| A61K 9/19 | (2006.01) |
| C07C 39/21 | (2006.01) |
| B82Y 5/00 | (2011.01) |

(52) U.S. Cl.
CPC .............. *C07C 37/84* (2013.01); *A61K 9/127* (2013.01); *A61K 9/19* (2013.01); *C07C 39/21* (2013.01); *B82Y 5/00* (2013.01); *C07B 2200/13* (2013.01)

(58) Field of Classification Search
CPC ......... C07C 37/84; C07C 39/21; A61K 9/127; A61K 9/19; A61K 31/05; A61K 47/26; C07B 2200/13
See application file for complete search history.

(56) References Cited

FOREIGN PATENT DOCUMENTS

| | | | |
|---|---|---|---|
| CN | 1895237 A | 1/2007 | |
| CN | 102070411 A | 5/2011 | |
| CN | 102351659 * | 2/2012 | ............. C07C 37/68 |
| CN | 104341272 A | 2/2015 | |
| CN | 109627147 A | 4/2019 | |
| CN | 111454127 A | 7/2020 | |
| KR | 20080016269 A | 2/2008 | |

OTHER PUBLICATIONS

Wu et al. ("Preparation of honokiol nanoparticles by liquid antisolvent precipitation technique, characterization, pharmacokinetics, and evaluation of inhibitory effect on HepG2 cells", International Journal of Medicine, vol. 13, 2018, pp. 5469-5483). (Year: 2018).*
Wang et al. ("Highly Water-Soluble Solid Dispersions of Honokiol: Preparation, Solubility, and Bioavailability Studies and Anti-Tumor Activity Evaluation", Pharmaceutics, vol. 11, Issue 11, Nov. 2019, 22 pages) (Year: 2019).*
Rajesh et al. ("Understanding DMSO/Water Interactions", The University of Texas at Austin University of Texas Libraries, 2017, 2 pages) (Year: 2017).*
Garza, B. et al., "Phytochemical investigation of Magnolia grandiflora green seed cones: Analytical and phytoceutical studies," Food Science and Nutrition, Mar. 7, 2019, pp. 1761-1767, vol. 7.
International Search Report for Application No. PCT/CN2021/072853 mailed Oct. 9, 2021, pp. 1-5.
Wang, D. et al., "Research progress on pharmacological effects of honokiol and its anti-tumor mechanism," Medical Recapitulate, Jun. 30, 2009, pp. 1725-1727, vol. 15, No. 11.

* cited by examiner

*Primary Examiner* — Rosalynd A Keys
(74) *Attorney, Agent, or Firm* — Lerner David LLP

(57) ABSTRACT

The present invention provides honokiol crystal forms A, B and C and amorphous form and a preparation method thereof, wherein the preparation method comprises dissolving honokiol in n-heptane and standing at room temperature overnight to obtain the separated crystal as honokiol crystal form A; heating the honokiol crystal form A and cooling to room temperature to obtain a solid as honokiol crystal form B; heating the honokiol crystal form A to the molten state and then standing at quenching temperature to obtain the separated crystal as honokiol crystal form C; and adding the honokiol crystal form A with an antisolvent in DMSO/H$_2$O system, and thus obtaining the oily matter as honokiol amorphous form. The honokiol crystal forms A, B and C and the amorphous form of the present invention have the advantages of good solubility, good stability, low hygroscopicity, long-term storage and/or good reproducibility, and are suitable for drug development.

24 Claims, 14 Drawing Sheets

HONOKIOL CRYSTAL FORMS, AMORPHOUS FORM AND PREPARATION THEREOF

CROSS-REFERENCE TO RELATED APPLICATIONS

This present application is a national phase entry under 35 U.S.C. § 371 of International Application No. PCT/CN2021/072853 filed Jan. 20, 2021, which claims priority from Chinese Patent Application No. 202011620565.1 filed Dec. 31, 2020, all of which are incorporated herein by reference in their entirety.

TECHNICAL FIELD

The invention relates to the medical field, in particular to honokiol crystal forms, amorphous form and preparation method thereof.

BACKGROUND

Honokiol, whose chemical name is 3',5-di-2-propenyl-1,1'-biphenyl-2,4'-diphenol, has the following structural formula:

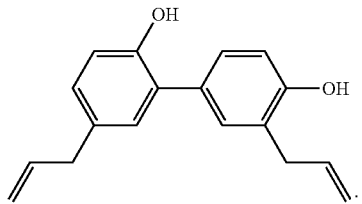

(I)

Honokiol, extracted from the bark of *Magnolia officinalis* Rehd. et Wils, is a small molecule compound with extensive biological activities. Its main biological activities include antimicrobial, antioxidant, anxiolytic, antidepressant, and antithrombotic activities. Recently, more and more studies have shown that honokiol has a good anti-tumor activity, and its antitumor effect is characterized by multiple targets, multiple effects and less toxic and side effects. Animal studies have shown that honokiol has a broad spectrum of anti-tumor activity against many kinds of rapidly growing tumors. It exerts anti-tumor effect by inducing tumor cell apoptosis, inhibiting migration and proliferation of tumor cells, and inhibiting tumor neovascularization.

The study of drug crystal form is one of the important contents in the study of new drugs. Therefore, it is of great significance to develop honokiol phase states with better physicochemical properties and bioavailability.

SUMMARY

An object of the present invention is to provide honokiol crystal forms superior in solubility, stability, hygroscopicity, etc.

In the first aspect of the present invention, a honokiol crystal form A is provided, hereinafter referred to as honokiol crystal form A, wherein the X-ray powder diffraction pattern of the honokiol crystal form A shows characteristic peaks at 2theta values of 6.79°±0.2°, 9.10°±0.2°, 13.97°±0.2°, 14.97°±0.2° and 17.54°±0.2° under Cu-Kα radiation.

Further, the X-ray powder diffraction pattern of the honokiol crystal form A of the present invention shows characteristic peaks at 2theta values of 6.79°±0.2°, 9.10°±0.2°, 13.97°±0.2°, 14.97°±0.2°, 17.54°±0.2°, 20.61°±0.2°, 22.08°±0.2°, 24.01°±0.2° under Cu-Kα radiation.

In a non-limiting manner, the honokiol crystal form A of the present invention has X-ray powder diffraction (XRPD) patterns as shown in FIG. 1, FIG. 3 to FIG. 9.

In a non-limiting manner, the honokiol crystal form A of the present invention has a thermogravimetric analysis (TGA)/differential scanning calorimetry (DSC) pattern as shown in FIG. 2.

The present invention also provides a preparation method for the honokiol crystal form A, comprising:

Method I: Preparing the Honokiol Crystal Form A by Recrystallization

Dissolving the honokiol in an organic solvent at 78° C. to 85° C. to obtain a honokiol solution, rapidly pouring the honokiol solution into another container, standing at room temperature overnight, centrifuging to collect the solids, and thus obtaining the honokiol crystal form A, wherein the organic solvent is n-heptane, petroleum ether, cyclohexane, n-hexane, toluene, DCM, DMSO, NMP, chloroform, methanol/water, or ethanol/water;

Method II: Preparing the Honokiol Crystal Form A by Gas-Solid Permeation

Placing the honokiol in a container, then adding an organic solvent to another container, placing the opened container containing the honokiol in the container containing organic solvent, sealing and standing at room temperature (until the surface of honokiol is slightly wet), centrifuging to collect the solids, and thus obtaining the honokiol crystal form A, wherein the organic solvent is ethyl acetate, isopropyl acetate, tert-butyl methyl ether, chloroform, N-methylpyrrolidone, ethanol or acetonitrile;

Method III: Preparing the Honokiol Crystal Form A by Gas-Liquid Permeation

Placing the honokiol in a container, dissolving in a solvent and filtering to obtain the clear honokiol solution, adding an antisolvent to another container, placing the opened container containing the clear honokiol solution in the container containing the antisolvent, sealing and standing at room temperature, centrifuging to collect the solids, and thus obtaining the honokiol crystal form A, wherein the solvent may be ethanol, tetrahydrofuran, chloroform, ethyl acetate or isopropanol, and the antisolvent may be n-hexane or water;

Method IV: Preparing the Honokiol Crystal Form A by Suspension Stirring at Room Temperature Placing the honokiol in a container, adding an organic solvent, magnetically stir the obtained suspension at room temperature, centrifuging to collect the solids, and thus obtaining the honokiol crystal form A, wherein the organic solvent may be methanol/water (94:6, 84:16, 69:31, 42:58), acetonitrile/water (1:9), acetone/water (1:9), or dichloromethane/n-hexane (1:9);

Method V: Preparing the Honokiol Crystal Form A by Suspension Stirring at 40-60° C.

Placing the honokiol in a container, adding an organic solvent, magnetically stir the obtained suspension at 40-60° C., centrifuging to collect the solids, and thus obtaining the honokiol crystal form A, wherein the organic solvent may be n-heptane, Tween/n-heptane (1:9), chloroform/n-heptane (1:9), or isopropanol/water (1:9);

Method VI: Preparing the Honokiol Crystal Form A by Temperature Cycling Stirring Placing the honokiol in a container, adding an organic solvent, magnetically stir the obtained suspension at temperature cycling, centrifuging to collect the solids, and thus obtaining the honokiol crystal form A, Where the temperature cycling includes 2 cycles of 60° C.→5° C., 0.1°C/min, and 5° C.→60° C., 1.5° C./min, and the preferred temperature cycling includes 2 cycles of 50° C.→5° C., 0.1° C./min, and 5° C.→50° C., 1.5° C./min, wherein the organic solvent may be n-heptane, ethanol/water (1:9), acetone/water (1:9), tetrahydrofuran/water (1:9), acetonitrile/water (1:9), ethyl acetate/n-heptane (1:9), tert-butyl methyl ether/n-hexane (1:9), or methyl isobutyl ketone/n-hexane (1:9);

Method VII: Preparing the Honokiol Crystal Form A by Slow Evaporation

Placing the honokiol in a container, dissolving in an organic solvent, filtering and taking the filtrate, sealing the container containing the filtrate with a sealing membrane, making several small holes on the sealing membrane, standing at room temperature to slowly volatilize, centrifuging to collect the solids, and thus obtaining the honokiol crystal form A, wherein the organic solvent may be chloroform, dichloromethane, methanol, isopropanol, or methyl isobutyl ketone;

Method VIII: Preparing the Honokiol Crystal Form A by Antisolvent Addition

Placing the honokiol in a container, dissolving in a solvent, adding an antisolvent under magnetic stirring, stirring while adding dropwise, standing, centrifuging to collect the solids, and thus obtaining the honokiol crystal form A, wherein the solvent may be ethanol, acetone, methyl isobutyl ketone, ethyl acetate, tert-butyl methyl ether, acetonitrile, dichloromethane or chloroform, and the antisolvent may be n-heptane or water.

In the second aspect of the present invention, a honokiol crystal form B is provided, hereinafter referred to as honokiol crystal form B, wherein the X-ray powder diffraction pattern of the honokiol crystal form B of the present invention shows characteristic peaks at 2theta values of 6.15°±0.2°, 6.76°±0.2°, 8.96°±0.2° and 15.90°±0.2° under Cu-Kα radiation.

Further, the X-ray powder diffraction pattern of the honokiol crystal form B of the present invention shows characteristic peaks at 2theta values of 6.15°±0.2°, 6.76°±0.2°, 8.96°±0.2°, 15.90°±0.2°, 17.49°±0.2° and 18.55°±0.2° under Cu-Kα radiation.

In a non-limiting manner, the honokiol crystal form B of the present invention has X-ray powder diffraction (XRPD) patterns as shown in FIG. 10, FIG. 12 to FIG. 15.

In a non-limiting manner, the honokiol crystal form B of the present invention has a thermogravimetric analysis (TGA)/differential scanning calorimetry (DSC) pattern as shown in FIG. 11.

The invention also provides a preparation method for the honokiol crystal form B, comprising the following steps of:
Heating the honokiol crystal form A to 80-82° C. and then cooling to the room temperature, and thus obtaining the solid as the honokiol crystal form B.

In the third aspect of the present invention, a honokiol crystal form C is provided, hereinafter referred to as honokiol crystal form C, wherein the X-ray powder diffraction pattern of the honokiol crystal form B of the present invention shows characteristic peaks at 2theta values of 14.04°±0.2°, 15.84°±0.2°, 17.42°±0.2° and 19.48°±0.2° under Cu-Kα radiation.

Further, the X-ray powder diffraction pattern of the honokiol crystal form B the present invention shows characteristic peaks at 2theta values of 14.04°±0.2°, 15.84°±0.2°, 17.42°±0.2°, 19.48°±0.2°, 21.26°±0.2°, 23.10°±0.2° and 24.06°±0.2° under Cu-Kα radiation.

In a non-limiting manner, the honokiol crystal form C of the present invention has X-ray powder diffraction (XRPD) patterns as shown in FIG. 16 and FIG. 18.

In a non-limiting manner, the honokiol crystal form C of the present invention has a thermogravimetric analysis (TGA)/differential scanning calorimetry (DSC) pattern as shown in FIG. 17.

The invention also provides a preparation method for the honokiol crystal form C, comprising the following steps of:
(1) Heating honokiol crystal form A to the molten state at 83-100° C. and stirring to mix thoroughly until no obvious particles are present;
(2) Placing the melt obtained in Step (1) rapidly at a quenching temperature of −20 to −196° C., and thus obtaining the separated crystal as the honokiol crystal form C.

Preferably, in the preparation methods of the honokiol crystal form C, the quenching temperature of Step (2) is −80 to −196° C.

In the fourth aspect of the present invention, a honokiol amorphous form is provided, which has good solubility and is suitable for the development of drug formulations.

In a non-limiting manner, the honokiol amorphous form of the present invention has X-ray powder diffraction (XRPD) patterns as shown in FIG. 19.

The invention also provides a preparation method for the honokiol amorphous form, comprising the following steps of:
(1) Dissolving the honokiol crystal form A in DMSO;
(2) Adding antisolvent water to the solution obtained in Step (1) and stirring;
(3) Centrifuging, discarding the supernatant, standing at room temperature, and thus obtaining an oily matter as the honokiol amorphous form.

Another object of the present invention is to provide a drug composition or drug product, comprising effective amounts of the honokiol crystal form A, the honokiol crystal form B, the honokiol crystal form C, or the honokiol amorphous form and pharmaceutical excipients. The drug composition or drug formulation is prepared in a manner well known in the pharmaceutical field, wherein the drug composition or drug formulation is prepared by mixing or contacting effective amounts of the honokiol crystal form A, the honokiol crystal form B, the honokiol crystal form C or the honokiol amorphous form with one or more pharmaceutical excipients.

A further object of the present invention is to provide a honokiol nano-liposome lyophilized powder, comprising effective amounts of the honokiol crystal form A, the honokiol crystal form B, the honokiol crystal form C, or the honokiol amorphous form. The honokiol nano-liposome lyophilized powder is prepared by the following method comprising dissolving the honokiol crystal form A, the honokiol crystal form B, the honokiol crystal form C or honokiol amorphous form (1 part), phospholipid (0.1-100 parts), phosphatidylethanolamine (0.01-100 parts) and cholesterol (0-100 parts) in absolute ethanol, injecting the solution that is completely dissolved into the purified water, stirring for rotary evaporation to remove the ethanol, adding the lyophilized excipient (1-50 parts), and thus obtaining the honokiol nano-liposome lyophilized powder by freeze-drying. After reconstitution of the lyophilized powder, the particle size of honokiol nano-liposome is 80-170 nm as determined by a laser particle analyzer.

The phospholipid is selected from one or more of soybean phospholipids, egg yolk lecithin, hydrogenated soybean lecithin, hydrogenated egg yolk lecithin, phosphatidylcholine, phosphatidylethanolamine, phosphatidylglycerol and sodium salts thereof, phosphatidylinositol, cardiolipin, sphingomyelin or phosphatidylserine; phosphatidylethanolamine is selected from one or more of the Cultured phosphatidylethanolamine, soybean phosphatidylethanolamine, distearyl phosphatidylethanolamine-polyethylene glycol$_{600-20000}$, dipalmitoyl phosphatidylethanolamine-polyethylene glycol$_{600-20000}$, dioleoylphosphatidylethanolamine-polyethylene glycol$_{600-20000}$, stearoyloleoylphosphatidylethanolamine-polyethylene glycol$_{600-20000}$, stearoylimidylphosphatidylethanolamine-polyethylene glycol$_{600-20000}$, palmitoylolcoylphosphatidylethanolamine-polyethylene glycol$_{600-20000}$, palmitoyl oleoylphosphatidylphosphatidyl ethanolamine-polyethylene glycol$_{600-20000}$, dimyristoylphosphatidylethanolamine-polyethylene glycol$_{600-20000}$, dilaurylphosphatidylethanolamine-polyethylene glycol$_{600-20000}$, didecanoyl phosphatidylethanolamine-polyethylene glycol$_{600-20000}$, dioctanoylphosphatidylethanolamine-polyethylene glycol 600-20000 or dihexanoylphosphatidylethanolamine-polyethylene glycol$_{600-20000}$; the excipients are selected from one or more of glucose, glycine, mannitol, inositol, sorbitol, sucrose, trehalose, lactose, galactose, glutamic acid, proline, lysine or alanine.

A further object of the present invention to provide the use of the honokiol crystal form A, the honokiol crystal form B, and the honokiol crystal form C or the honokiol Amorphous form in the preparation of drugs for the treatment of tumors.

A further object of the present invention is to provide the use of the honokiol crystal form A, the honokiol crystal form B, the honokiol crystal form C or the honokiol amorphous form in preparation of drugs for the treatment of tumors.

The honokiol crystal forms A, B and C of the present invention have the advantages of good solubility, good stability, low hygroscopicity, long-term storage and good reproducibility, and are suitable for drug development; the honokiol amorphous form of the present invention has good amorphous solubility and is suitable for the development of drug products.

DETAILED DESCRIPTION

The following embodiments further illustrate the present invention, however, they do not constitute a restrictions or limitation of the scope of the invention.

Reagents used in embodiments of the present invention are conventional reagents in the field. Unless otherwise specified hereinafter, the reagents used in the present invention are well known in the field, but they are described in the present invention in detail as much as possible.

Raw materials used in the embodiment and the preparation method of honokiol powder are detailed in Journal of Chromatography A, 1142 (2007) 115-122.

Figure 1:
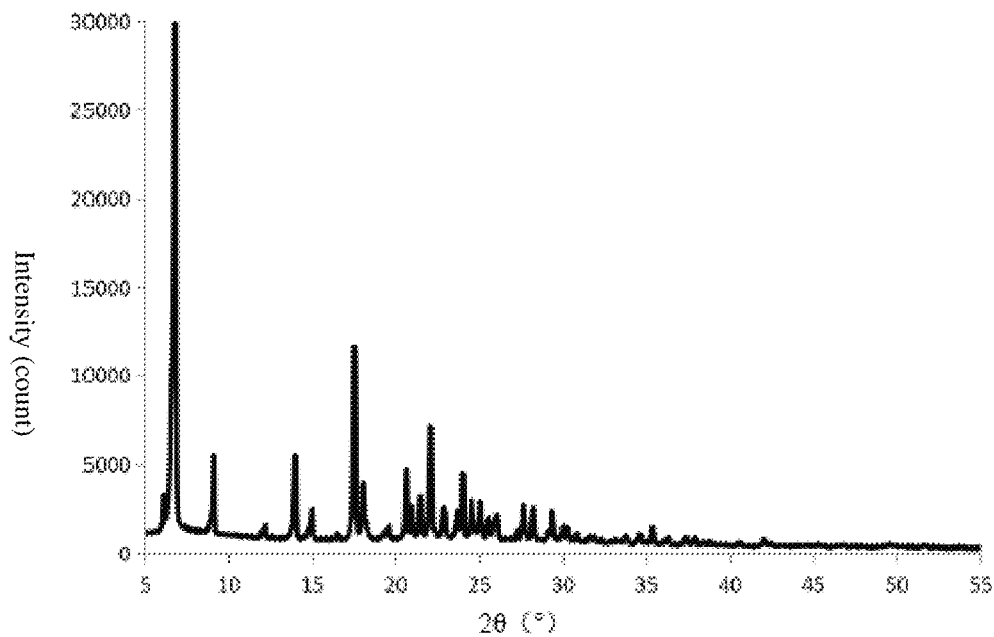
FIG. 1 is an XRPD pattern of the honokiol crystal form A in embodiment 1.
Figure 2:
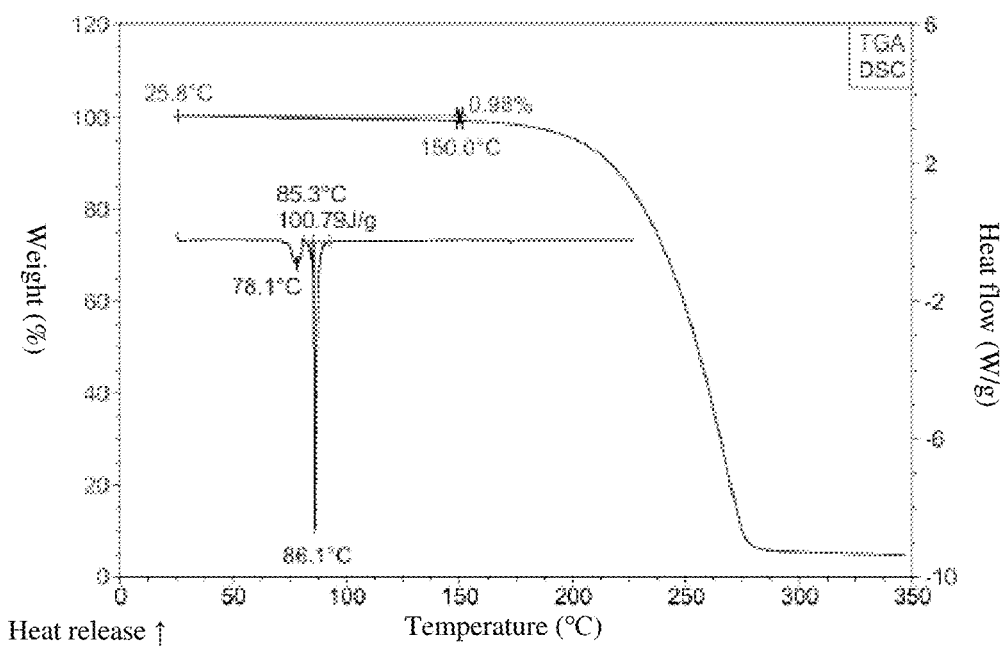
FIG. 2 is an TGA/DSC pattern of the honokiol crystal form A in embodiment 1.

Embodiment 1: Preparing the Honokiol Crystal Form A by Recrystallization with n-Heptane Dissolving 201.25 mg honokiol powder completely in n-heptane at 80° C., then pouring the solution to another beaker quickly, standing at the room temperature overnight, and thus obtaining the crystals as the honokiol crystal form A, of which the XRPD pattern is shown in FIG. 1 and the TGA/DSC pattern is shown in FIG. 2.

The corresponding values of 2theta values and intensities of the honokiol crystal form A in the embodiment are shown in Table 1:

TABLE 1

Corresponding Values of 2theta Values and Intensities of the Honokiol Crystal Form A

| No. | 2theta | Intensity % |
|---|---|---|
| 1 | 6.0935 | 4.95 |
| 2 | 6.5328 | 16.41 |
| 3 | 6.7971 | 100 |
| 4 | 9.1031 | 9.68 |
| 5 | 12.1559 | 2.25 |
| 6 | 13.9719 | 9.78 |
| 7 | 14.9720 | 4.12 |
| 8 | 16.5075 | 1.41 |
| 9 | 17.5405 | 21.51 |
| 10 | 19.3106 | 1.6 |
| 11 | 19.5697 | 2.11 |
| 12 | 20.6195 | 8.33 |
| 13 | 20.9485 | 4.39 |
| 14 | 21.4800 | 5.3 |
| 15 | 22.0843 | 12.89 |
| 16 | 22.8333 | 4.1 |
| 17 | 22.9755 | 3.79 |
| 18 | 23.7021 | 3.91 |
| 19 | 24.0117 | 7.96 |
| 20 | 24.5432 | 4.73 |
| 21 | 25.0433 | 4.66 |
| 22 | 25.5378 | 3.06 |
| 23 | 25.8289 | 2.58 |
| 24 | 26.0495 | 3.15 |
| 25 | 27.2453 | 1.76 |
| 26 | 27.6398 | 4.35 |
| 27 | 28.2230 | 4.18 |
| 28 | 29.0779 | 1.63 |
| 29 | 29.3534 | 3.65 |
| 30 | 30.0155 | 2.14 |
| 31 | 30.3107 | 2 |
| 32 | 30.8450 | 1.41 |
| 33 | 31.5797 | 1.11 |
| 34 | 31.8736 | 1.12 |
| 35 | 33.7018 | 1.18 |
| 36 | 34.6063 | 1.37 |
| 37 | 35.3406 | 2.01 |
| 38 | 36.2867 | 0.91 |
| 39 | 37.4284 | 0.98 |
| 40 | 37.8896 | 0.88 |
| 41 | 38.7965 | 0.59 |
| 42 | 40.5974 | 0.49 |
| 43 | 42.0185 | 0.79 |
| 44 | 45.2149 | 0.3 |
| 45 | 49.5154 | 0.29 |
| 46 | 51.6076 | 0.21 |

Embodiment 2: Preparing the Honokiol Crystal Form A by Gas-Solid Permeation

Figure 3:
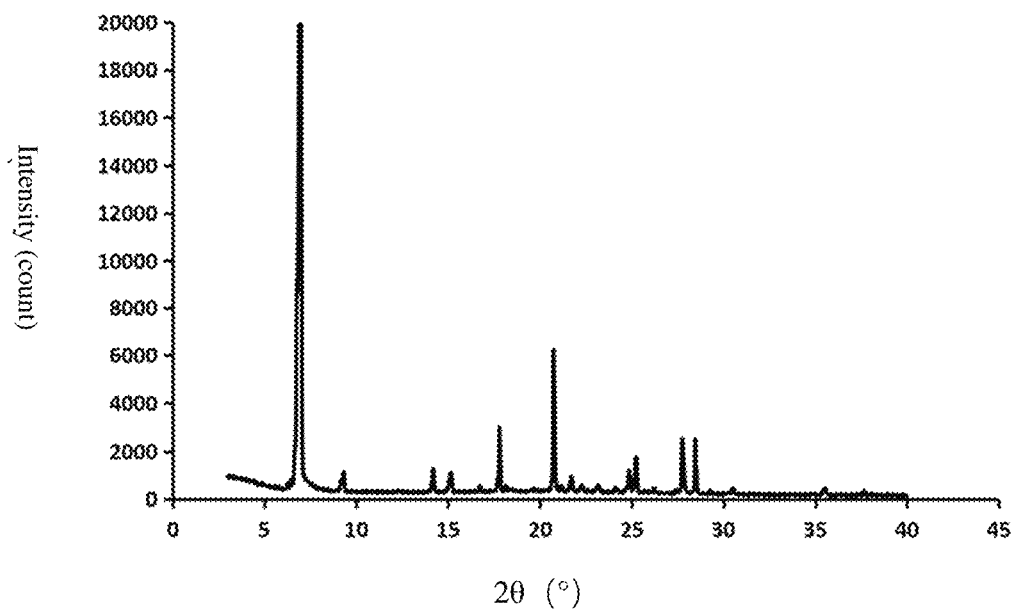
FIG. 3 is an XRPD pattern of the honokiol crystal form A in embodiment 2.

Weighing about 15 mg of honokiol powder into a 3 mL vial, adding about 3 mL of N-methylpyrrolidone into another 20 mL vial, placing the 3 mL opened vial in the 20 mL vial and sealing the 20 mL vial. Standing at room temperature until the surface of honokiol is slightly wet, centrifuging to collect the solids, and thus obtaining the honokiol crystal form A. The obtained solid is the honokiol crystal form A as confirmed by an XRPD test, of which the XRPD pattern is shown in FIG. 3, and the TGA/DSC pattern is consistent with the TGA/DSC pattern of the honokiol crystal form A prepared in embodiment 1.

Figure 4:
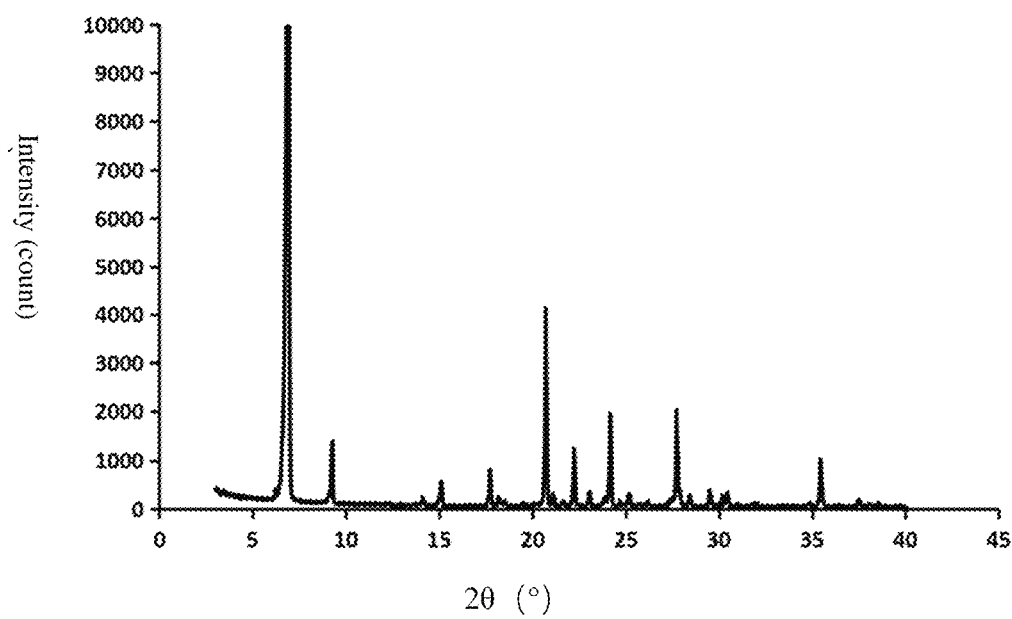
FIG. 4 is an XRPD pattern of the honokiol crystal form A in embodiment 3.

Embodiment 3: Preparing the Honokiol Crystal Form A by Gas-Liquid Permeation Weighing about 15 mg of honokiol powder into a 3 mL vial, dissolving in 0.5 mL of isopropanol and filtering through a 0.45 μm PTFE membrane to obtain a clear solution; adding about 3 mL of antisolvent water to another 20 mL vial, placing the 3 mL opened vial containing the clear solution in the 20 mL vial, sealing the 20 mL vial and standing at the room temperature for 9 days. Centrifuging to collect the solids, and thus obtaining the honokiol crystal form A. The obtained solid is the honokiol crystal form A as confirmed by an XRPD test, of which the XRPD pattern is shown in FIG. 4, and the TGA/DSC pattern is consistent with the TGA/DSC pattern of the honokiol crystal form A prepared in embodiment 1.

Figure 5:
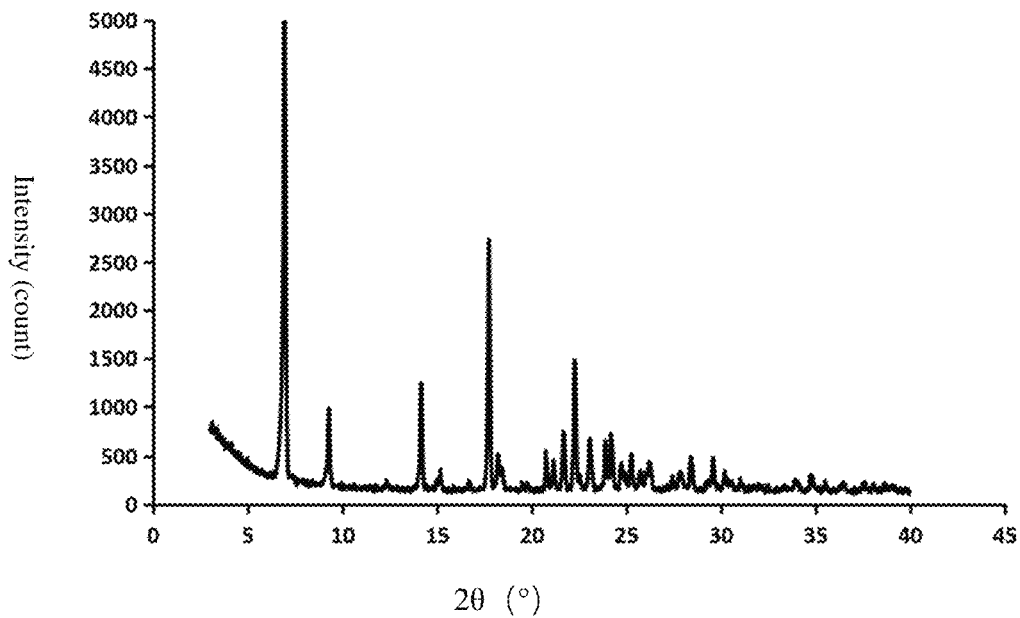
FIG. 5 is an XRPD pattern of the honokiol crystal form A in embodiment 4.

Embodiment 4: Preparing the Honokiol Crystal Form A by Suspension Stirring at Room Temperature Weighing about 15 mg honokiol powder into a 3 mL vial, adding 0.3-0.5 mL of acetonitrile/water (1:9), magnetically stirring the obtained suspension at the room temperature for 4 days, centrifuging to collect the solids, and thus obtaining the honokiol crystal form A. The obtained solid is the honokiol crystal form A as confirmed by an XRPD test, of which the XRPD pattern is shown in FIG. 5, and the TGA/DSC pattern is consistent with the TGA/DSC pattern of the honokiol crystal form A prepared in embodiment 1.

Embodiment 5: Preparing the Honokiol Crystal Form A by Suspension Stirring at 50° C.

Figure 6:
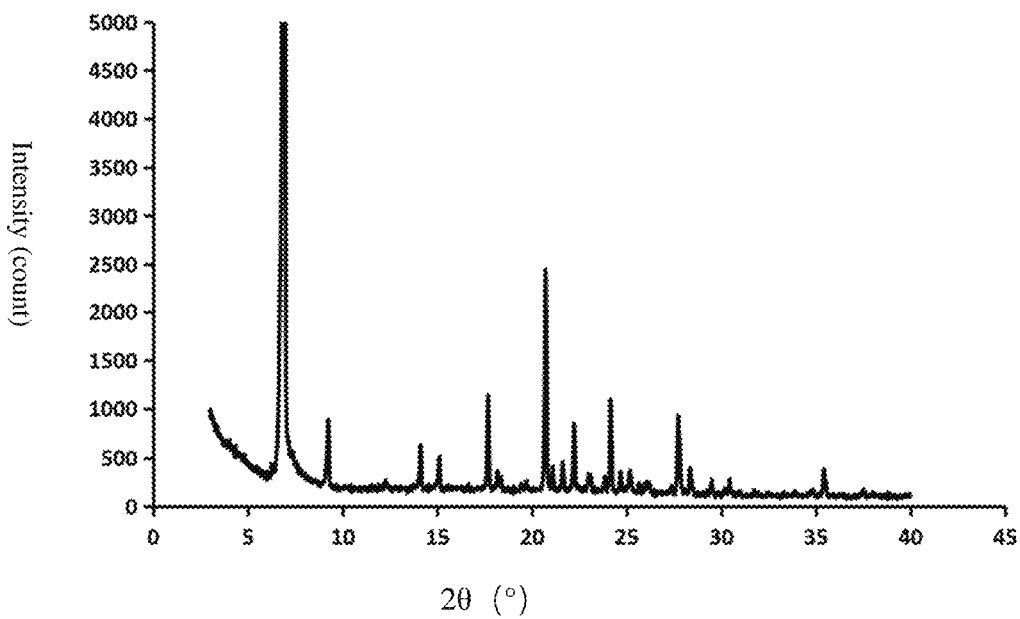
FIG. 6 is an XRPD pattern of the honokiol crystal form A in embodiment 5.

Weighing about 15 mg of honokiol powder into a 3 mL vial, adding 0.5 mL of chloroform/n-heptane (1:9), magnetically stirring the obtained suspension below 50° C. and at 1000 rpm for 4 days, centrifuging to collect the solids, and thus obtaining the honokiol crystal form A. The obtained solid is the honokiol crystal form A as confirmed by an XRPD test, of which the XRPD pattern is shown in FIG. 6, and the TGA/DSC pattern is consistent with the TGA/DSC pattern of the honokiol crystal form A prepared in embodiment 1.

Figure 7:
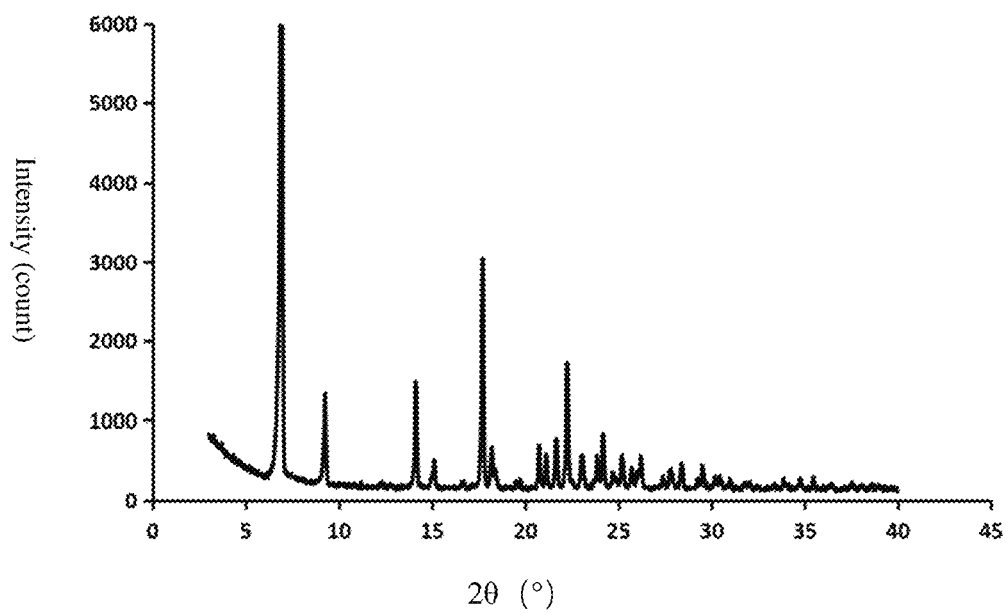
FIG. 7 is an XRPD pattern of the honokiol crystal form A in embodiment 6.

Embodiment 6: Preparing the Honokiol Crystal Form a by Temperature Cycling Stirring Weighing about 15 mg of honokiol powder into a 3 ml, vial, adding 0.5 mL of ethanol/water (1:9), magnetically stirring the obtained suspension at the temperature cycling (2 cycles including 50° C.→5° C., 0.1° C./min, and 5° C.→50° C., 1.5° C./min) and at 1000 rpm for 16 h, centrifuging to collect the solids, and thus obtaining the honokiol crystal form A. The obtained solid is the honokiol crystal form A as confirmed by an XRPD test, of which the XRPD pattern is shown in FIG. 7, and the TGA/DSC pattern is consistent with the TGA/DSC pattern of the honokiol crystal form A prepared in embodiment 1.

Embodiment 7: Preparing the Honokiol Crystal Form A by Slow Volatilization

Figure 8:
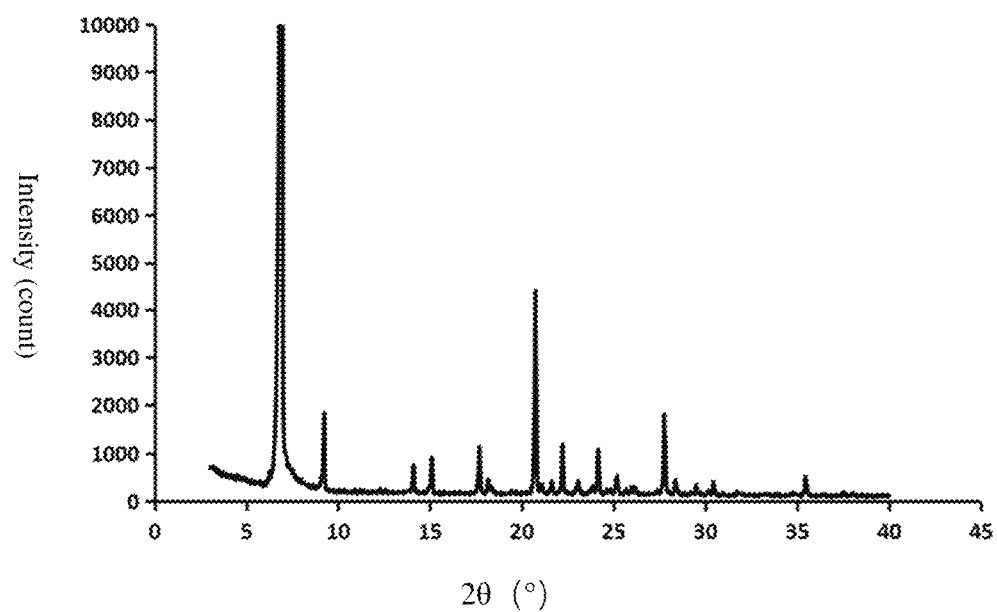
FIG. 8 is an XRPD pattern of the honokiol crystal form A in embodiment 7.

Weighing about 15 mg of honokiol powder into a 3 mL vial, dissolving in 1.0 ml of chloroform, filtering (with PTFE membrane with a pore size of 0.45 μm) and taking the filtrate. Scaling the vial containing clear solution with a sealing membrane, making several small holes on the scaling membrane, standing at room temperature to slowly volatilize for separation of solids, centrifuging to collect the solids, and thus obtaining the honokiol crystal form A. The obtained solid is the honokiol crystal form A as confirmed by an XRPD test, of which the XRPD pattern is shown in FIG. 8, and the TGA/DSC pattern is consistent with the TGA/DSC pattern of the honokiol crystal form A prepared in embodiment 1.

Embodiment 8: Preparing the Honokiol Crystal Form A by Antisolvent Addition

Figure 9:
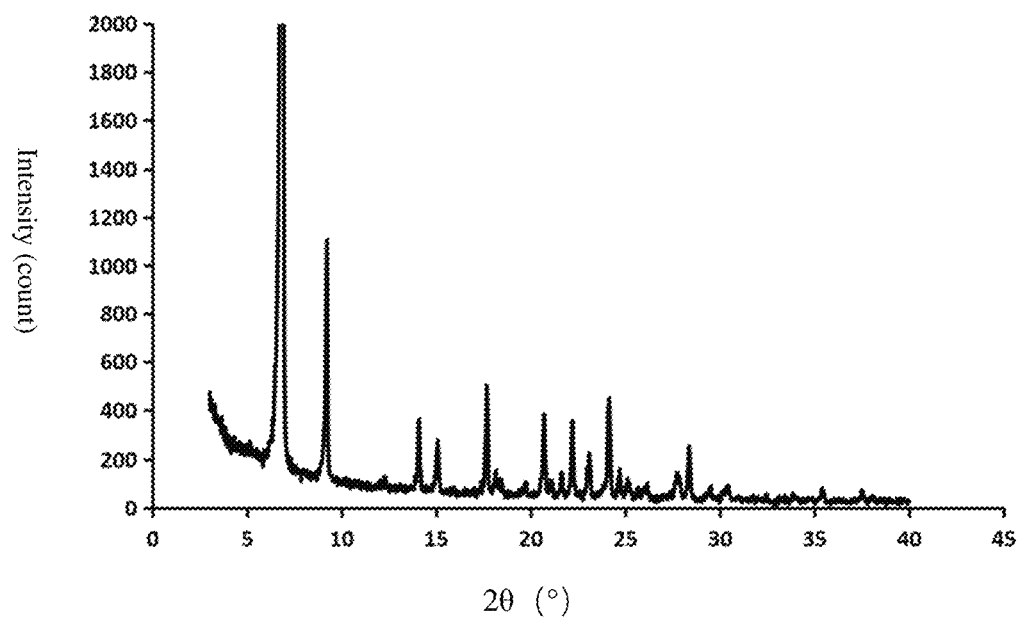
FIG. 9 is an XRPD pattern of the honokiol crystal form A in embodiment 8.

Weighing about 15 mg of honokiol powder into a 3 mL vial, dissolving in 0.5-1.0 ml of ethanol, adding n-heptane under magnetic stirring, stirring while adding dropwise, standing overnight, centrifuging to collect the solids, and thus obtaining the honokiol crystal form A. The obtained solid is the honokiol crystal form A as confirmed by an XRPD test, of which the XRPD pattern is shown in FIG. 9, and the TGA/DSC pattern is consistent with the TGA/DSC pattern of the honokiol crystal form A prepared in embodiment 1.

Embodiment 9: Preparation of the Honokiol Crystal Form B

Figure 10:
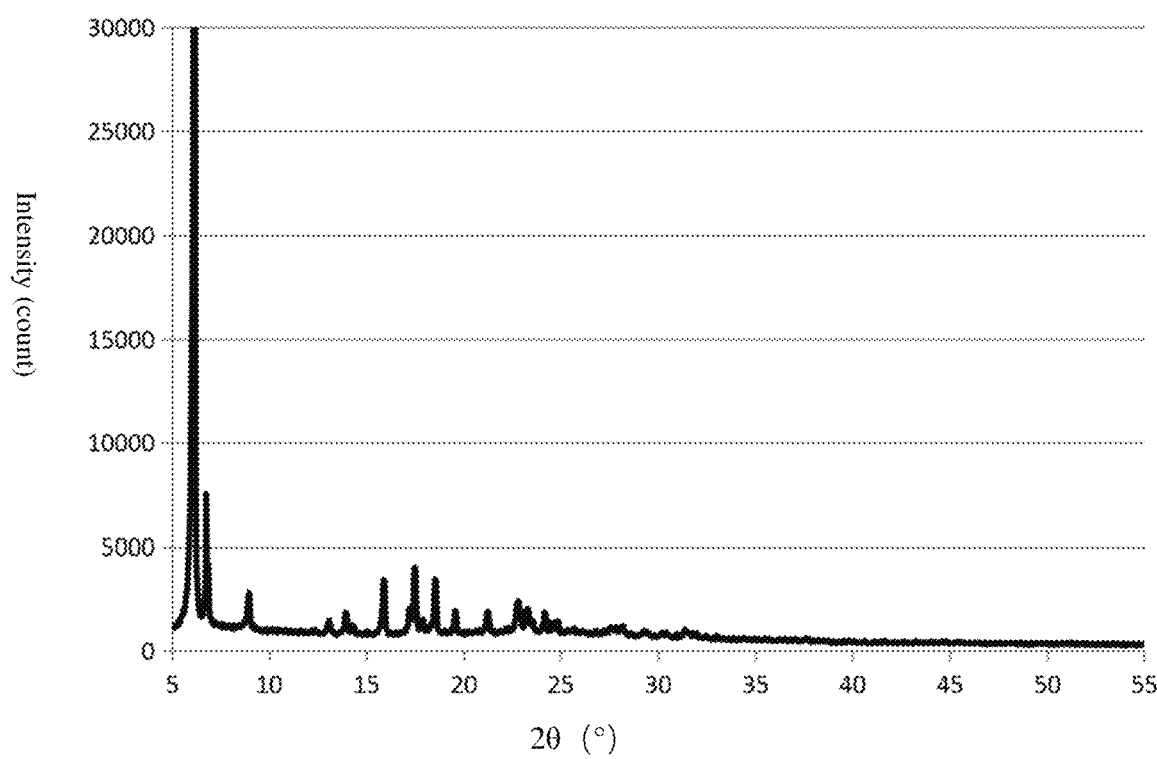
FIG. 10 is an XRPD pattern of the honokiol crystal form B treated after cooling to the room temperature immediately after heating to 80° C. in embodiment 9.
Figure 11:
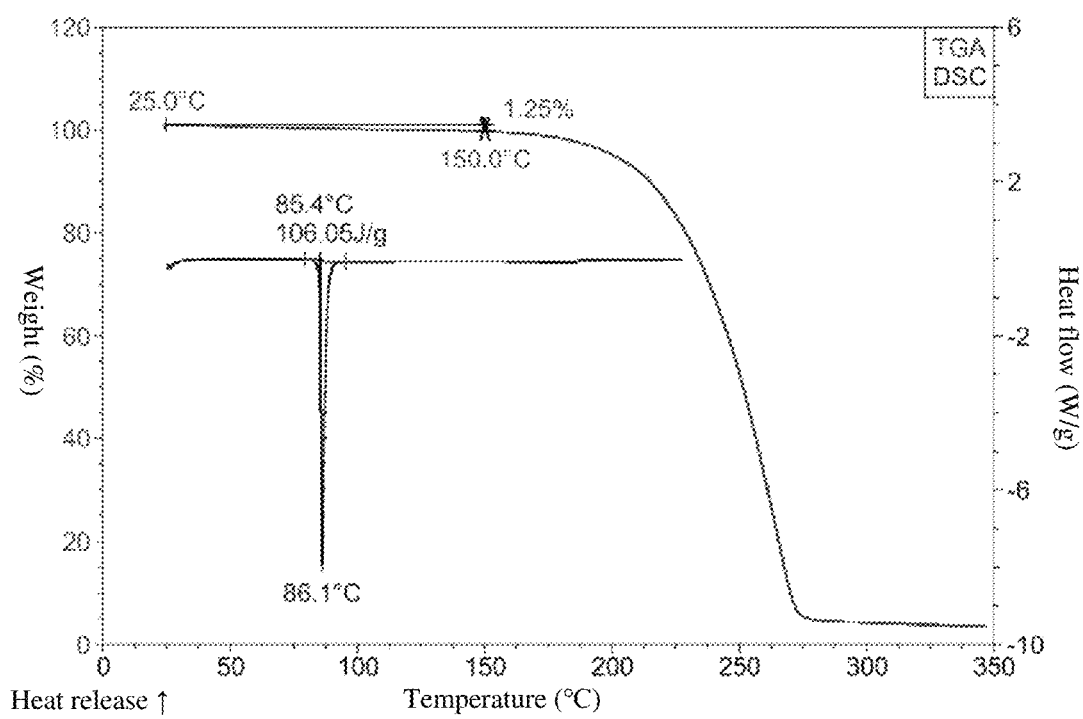
FIG. 11 is a TGA/DSC pattern of the honokiol crystal form B treated after cooling to the room temperature immediately after heating to 80° C. in embodiment 9.

Placing the sample at the room temperature immediately after heating 200.75 mg of honokiol crystal form A to 80° C., and thus obtaining the solid as the honokiol crystal form B, of which the XRPD spectrum is shown in FIG. 10 and the TGA/DSC pattern is shown in FIG. 11.

The corresponding values of 2theta values and intensities of the honokiol crystal form B in the embodiment are shown in Table 2:

TABLE 2

Corresponding Values of 2theta Values and Intensities of the Honokiol Crystal Form B

| No. | 2theta | Intensity % |
|---|---|---|
| 1 | 6.1504 | 100.00 |
| 2 | 6.7608 | 15.08 |
| 3 | 8.9653 | 4.93 |
| 4 | 13.0808 | 1.88 |
| 5 | 13.9526 | 2.77 |
| 6 | 14.3170 | 1.39 |
| 7 | 15.9024 | 6.34 |
| 8 | 17.2149 | 3.10 |
| 9 | 17.4955 | 7.62 |
| 10 | 17.9023 | 2.02 |
| 11 | 18.5502 | 6.26 |
| 12 | 19.5855 | 2.79 |
| 13 | 21.2438 | 2.88 |
| 14 | 22.7821 | 4.06 |
| 15 | 23.2199 | 2.99 |
| 16 | 23.5529 | 1.90 |
| 17 | 24.1781 | 2.76 |
| 18 | 24.5335 | 1.66 |

TABLE 2-continued

Corresponding Values of 2theta Values and Intensities of the Honokiol Crystal Form B

| No. | 2theta | Intensity % |
|---|---|---|
| 19 | 24.8318 | 1.84 |
| 20 | 26.7765 | 0.88 |
| 21 | 28.1861 | 1.33 |
| 22 | 29.3438 | 0.75 |
| 23 | 30.3149 | 0.58 |
| 24 | 31.3429 | 0.99 |
| 25 | 31.9348 | 0.60 |
| 26 | 37.6766 | 0.24 |

Embodiment 10: Preparation of the Honokiol Crystal Form B

Figure 12:
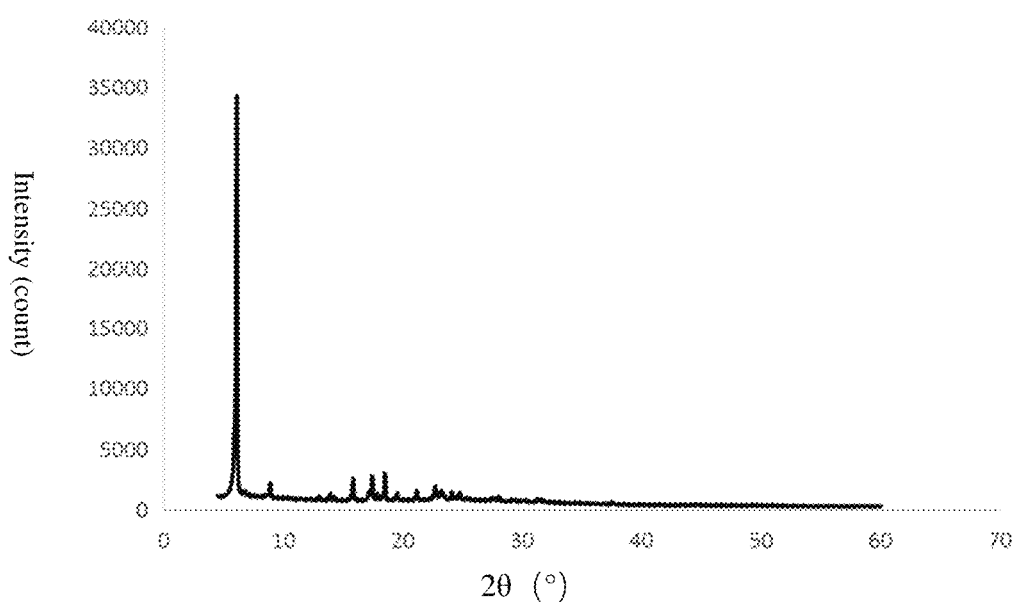
FIG. 12 is an XRPD pattern of the honokiol crystal form B treated after heating to 80° C. and holding for 1 h and then cooling to the room temperature in embodiment 10.

Placing the sample at the room temperature immediately after heating 200.65 mg of honokiol crystal form A to 80° C. and holding for 1 h, and thus obtaining the solid as the honokiol crystal form B, of which the XRPD spectrum is shown in FIG. 12, and the TGA/DSC pattern is consistent with the TGA/DSC spectrum of the honokiol crystal form B prepared in embodiment 9.

The corresponding values of 2theta values and intensities of the honokiol crystal form B in the embodiment are shown in Table 3:

TABLE 3

Corresponding Values of 2theta Values and Intensities of the Honokiol Crystal Form B

| No. | 2theta | Intensity % |
|---|---|---|
| 1 | 6.1145 | 100 |
| 2 | 8.9191 | 4.83 |
| 3 | 13.0492 | 1.62 |
| 4 | 13.9199 | 2.4 |
| 5 | 14.2635 | 1.4 |
| 6 | 15.8646 | 6.33 |
| 7 | 17.1657 | 2.82 |
| 8 | 17.4554 | 6.9 |
| 9 | 17.8548 | 2.25 |
| 10 | 18.5209 | 7.66 |
| 11 | 19.5406 | 2.55 |
| 12 | 21.1944 | 2.98 |
| 13 | 22.733 | 4.21 |
| 14 | 23.1809 | 2.91 |
| 15 | 24.1315 | 2.66 |
| 16 | 24.7949 | 2.72 |
| 17 | 25.5231 | 1.15 |
| 18 | 28.0686 | 1.32 |
| 19 | 31.3283 | 1.03 |
| 20 | 37.6203 | 0.39 |

Embodiment 11: Preparation of the Honokiol Crystal Form B

Figure 13:
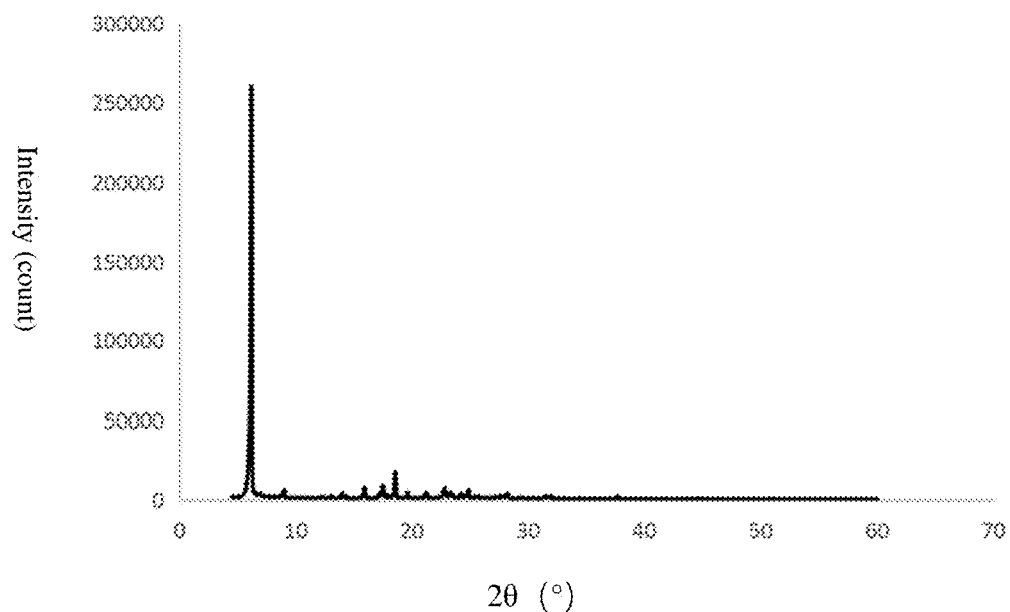
FIG. 13 is an XRPD pattern of the honokiol crystal form B treated after heating to 80° C. and holding for 4 h and then cooling to the room temperature in embodiment 11.

Placing the sample at the room temperature immediately after heating 200.25 mg of honokiol crystal form A to 80° C. and holding for 4 h, and thus obtaining the solid as the honokiol crystal form B, of which the XRPD spectrum is shown in FIG. 13, and the TGA/DSC pattern is consistent with the TGA/DSC spectrum of the honokiol crystal form B prepared in embodiment 9.

The corresponding values of 2theta values and intensities of the honokiol crystal form B in the embodiment are shown in Table 4:

TABLE 4

Corresponding Values of 2theta Values and
Intensities of the Honokiol Crystal Form B

| No. | 2theta | Intensity % |
|---|---|---|
| 1 | 6.1917 | 100 |
| 2 | 6.906 | 1.62 |
| 3 | 9.0082 | 2.3 |
| 4 | 12.3598 | 0.69 |
| 5 | 13.1118 | 0.79 |
| 6 | 13.9898 | 1.53 |
| 7 | 14.3439 | 0.65 |
| 8 | 15.9382 | 2.9 |
| 9 | 17.242 | 1.41 |
| 10 | 17.5357 | 3.32 |
| 11 | 17.9295 | 1.17 |
| 12 | 18.5849 | 6.77 |
| 13 | 19.6136 | 1.71 |
| 14 | 21.2758 | 1.66 |
| 15 | 22.796 | 2.94 |
| 16 | 23.3027 | 1.77 |
| 17 | 23.5706 | 0.92 |
| 18 | 24.211 | 1.3 |
| 19 | 24.5713 | 0.89 |
| 20 | 24.8569 | 2.3 |
| 21 | 25.7046 | 0.69 |
| 22 | 26.8102 | 0.51 |
| 23 | 27.5878 | 0.83 |
| 24 | 27.846 | 0.82 |
| 25 | 28.1965 | 1.3 |
| 26 | 29.2644 | 0.48 |
| 27 | 29.4753 | 0.48 |
| 28 | 30.4566 | 0.43 |
| 29 | 31.4005 | 0.71 |
| 30 | 31.9042 | 0.74 |
| 31 | 32.4824 | 0.32 |
| 32 | 33.0914 | 0.35 |
| 33 | 34.4144 | 0.23 |
| 34 | 37.6543 | 0.67 |
| 35 | 40.0415 | 0.16 |
| 36 | 41.6417 | 0.12 |
| 37 | 44.2058 | 0.11 |
| 38 | 44.6725 | 0.24 |
| 39 | 45.4141 | 0.1 |
| 40 | 46.396 | 0.08 |
| 41 | 49.6005 | 0.06 |
| 42 | 50.9781 | 0.15 |

Embodiment 12: Preparation of the Honokiol Crystal Form B

Figure 14:
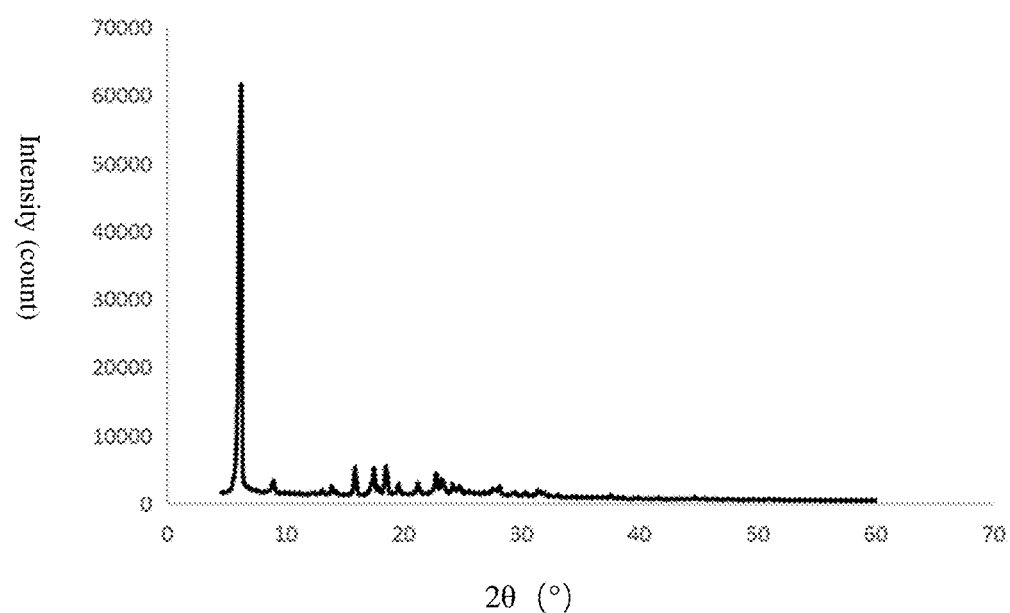
FIG. 14 is an XRPD pattern of the honokiol crystal form B treated after heating to 80° C. and holding for 8 h and then cooling to the room temperature in embodiment 12.

Placing the sample at the room temperature immediately after heating 201.25 mg of honokiol crystal form A to 80° C. and holding for 8 h, and thus obtaining the solid as the honokiol crystal form B, of which the XRPD spectrum is shown in FIG. 14, and the TGA/DSC pattern is consistent with the TGA/DSC spectrum of the honokiol crystal form B prepared in embodiment 9.

The corresponding values of 2theta values and intensities of the honokiol crystal form B in the embodiment are shown in Table 5:

TABLE 5

Corresponding Values of 2theta Values and
Intensities of the Honokiol Crystal Form B

| No. | 2theta | Intensity % |
|---|---|---|
| 1 | 6.0859 | 89.22 |
| 2 | 6.2586 | 100 |
| 3 | 8.9298 | 4.87 |
| 4 | 12.3175 | 1.75 |
| 5 | 13.0913 | 2.39 |

TABLE 5-continued

Corresponding Values of 2theta Values and
Intensities of the Honokiol Crystal Form B

| No. | 2theta | Intensity % |
|---|---|---|
| 6 | 13.9301 | 3.52 |
| 7 | 14.4509 | 1.84 |
| 8 | 15.8914 | 7.98 |
| 9 | 17.1827 | 3.65 |
| 10 | 17.4718 | 8.24 |
| 11 | 17.8736 | 3.23 |
| 12 | 18.4936 | 8.26 |
| 13 | 18.6688 | 5.88 |
| 14 | 19.5528 | 4.02 |
| 15 | 21.2134 | 4.17 |
| 16 | 22.7336 | 6.36 |
| 17 | 23.309 | 5.07 |
| 18 | 23.551 | 3.42 |
| 19 | 24.1664 | 4.01 |
| 20 | 24.491 | 2.68 |
| 21 | 24.7726 | 3.54 |
| 22 | 25.6034 | 2.24 |
| 23 | 26.7734 | 1.89 |
| 24 | 27.5516 | 2.85 |
| 25 | 28.1247 | 3.39 |
| 26 | 29.4852 | 1.76 |
| 27 | 30.349 | 1.66 |
| 28 | 31.3386 | 2.25 |
| 29 | 31.9246 | 1.77 |
| 30 | 33.0757 | 1.12 |
| 31 | 34.4329 | 0.88 |
| 32 | 37.5659 | 1.08 |
| 33 | 39.9031 | 0.49 |
| 34 | 41.5763 | 0.43 |
| 35 | 44.6686 | 0.66 |
| 36 | 45.4135 | 0.37 |
| 37 | 46.3251 | 0.3 |
| 38 | 47.6436 | 0.24 |
| 39 | 49.5829 | 0.18 |
| 40 | 50.9185 | 0.28 |

Embodiment 13: Preparation of the Honokiol Crystal Form B

Figure 15:
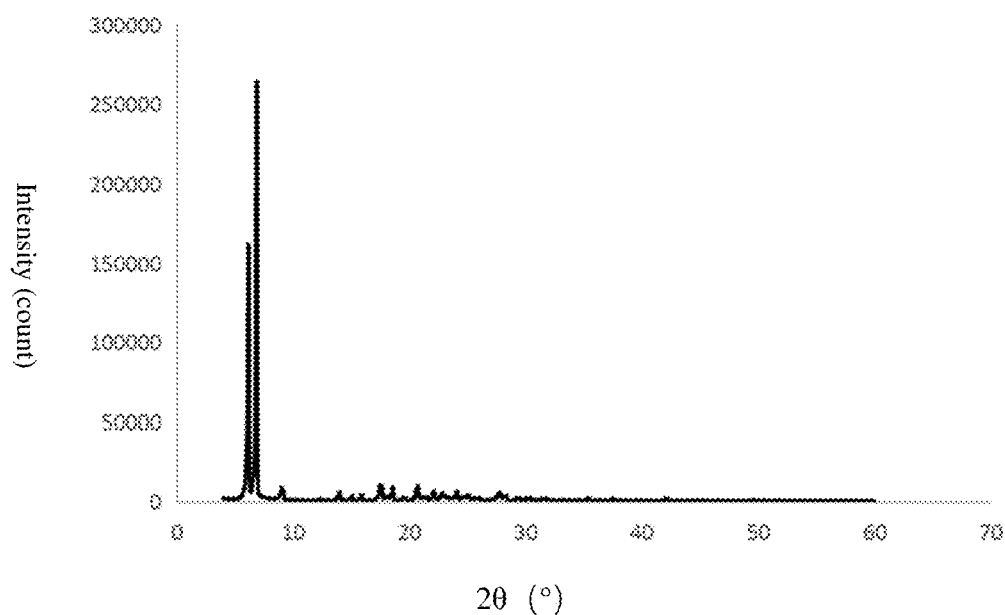
FIG. 15 is an XRPD pattern of the honokiol crystal form B treated after cooling to room temperature immediately after heating to 82° C. in embodiment 13.

Placing the sample at the room temperature immediately after heating 200.15 mg of honokiol crystal form A to 82° C., and thus obtaining the solid as the honokiol crystal form B, of which the XRPD spectrum is shown in FIG. 15, and the TGA/DSC pattern is consistent with the TGA/DSC spectrum of the honokiol crystal form B prepared in embodiment 9.

The corresponding values of 2theta values and intensities of the honokiol crystal form B in the embodiment are shown in Table 6:

TABLE 6

Corresponding Values of 2theta Values and
Intensities of the Honokiol Crystal Form B

| No. | 2theta | Intensity % |
|---|---|---|
| 1 | 6.1607 | 59.56 |
| 2 | 6.5174 | 4.42 |
| 3 | 6.8724 | 100 |
| 4 | 9.0088 | 2.83 |
| 5 | 9.1692 | 2.01 |
| 6 | 12.2552 | 0.15 |
| 7 | 13.0794 | 0.21 |
| 8 | 14.006 | 1.83 |
| 9 | 14.2782 | 0.18 |
| 10 | 15.0641 | 1.05 |
| 11 | 15.9119 | 1.2 |
| 12 | 16.5522 | 0.02 |

TABLE 6-continued

Corresponding Values of 2theta Values and
Intensities of the Honokiol Crystal Form B

| No. | 2theta | Intensity % |
|---|---|---|
| 13 | 17.2202 | 0.8 |
| 14 | 17.4603 | 3.35 |
| 15 | 17.6241 | 3.47 |
| 16 | 17.9209 | 0.63 |
| 17 | 18.1087 | 0.95 |
| 18 | 18.5873 | 2.86 |
| 19 | 19.4273 | 0.48 |
| 20 | 19.6235 | 0.56 |
| 21 | 20.5742 | 2.29 |
| 22 | 20.7317 | 3.11 |
| 23 | 21.0086 | 0.44 |
| 24 | 21.2764 | 0.5 |
| 25 | 21.4974 | 0.46 |
| 26 | 22.0504 | 1.83 |
| 27 | 22.7693 | 1.11 |
| 28 | 23.2588 | 0.34 |
| 29 | 23.9398 | 0.89 |
| 30 | 24.1083 | 1.51 |
| 31 | 24.5834 | 0.41 |
| 32 | 24.8612 | 0.65 |
| 33 | 25.1094 | 0.98 |
| 34 | 25.5801 | 0.25 |
| 35 | 25.9375 | 0.42 |
| 36 | 27.6025 | 1.62 |
| 37 | 27.7528 | 1.62 |
| 38 | 28.0915 | 0.81 |
| 39 | 28.3164 | 0.99 |
| 40 | 29.3251 | 0.53 |
| 41 | 29.9711 | 0.25 |
| 42 | 30.4174 | 0.5 |
| 43 | 30.8365 | 0.03 |
| 44 | 31.3583 | 0.17 |
| 45 | 31.6421 | 0.29 |
| 46 | 31.9099 | 0.2 |
| 47 | 32.3041 | 0.06 |
| 48 | 33.1748 | 0.13 |
| 49 | 33.7905 | 0.13 |
| 50 | 34.4223 | 0.11 |
| 51 | 35.4539 | 0.53 |
| 52 | 36.381 | 0.12 |
| 53 | 37.4516 | 0.32 |
| 54 | 38.7171 | 0.05 |
| 55 | 39.5517 | 0.21 |
| 56 | 40.4904 | 0.03 |
| 57 | 42.0234 | 0.46 |
| 58 | 43.1904 | 0.04 |
| 59 | 44.0785 | 0.06 |
| 60 | 44.6456 | 0.13 |
| 61 | 45.3062 | 0.06 |
| 62 | 46.4142 | 0.09 |
| 63 | 47.6515 | 0.02 |
| 64 | 49.4697 | 0.18 |
| 65 | 51.7075 | 0.16 |
| 66 | 53.7499 | 0.04 |
| 67 | 57.3282 | 0.02 |

Embodiment 14: Preparation of the Honokiol Crystal Form C

Figure 16:
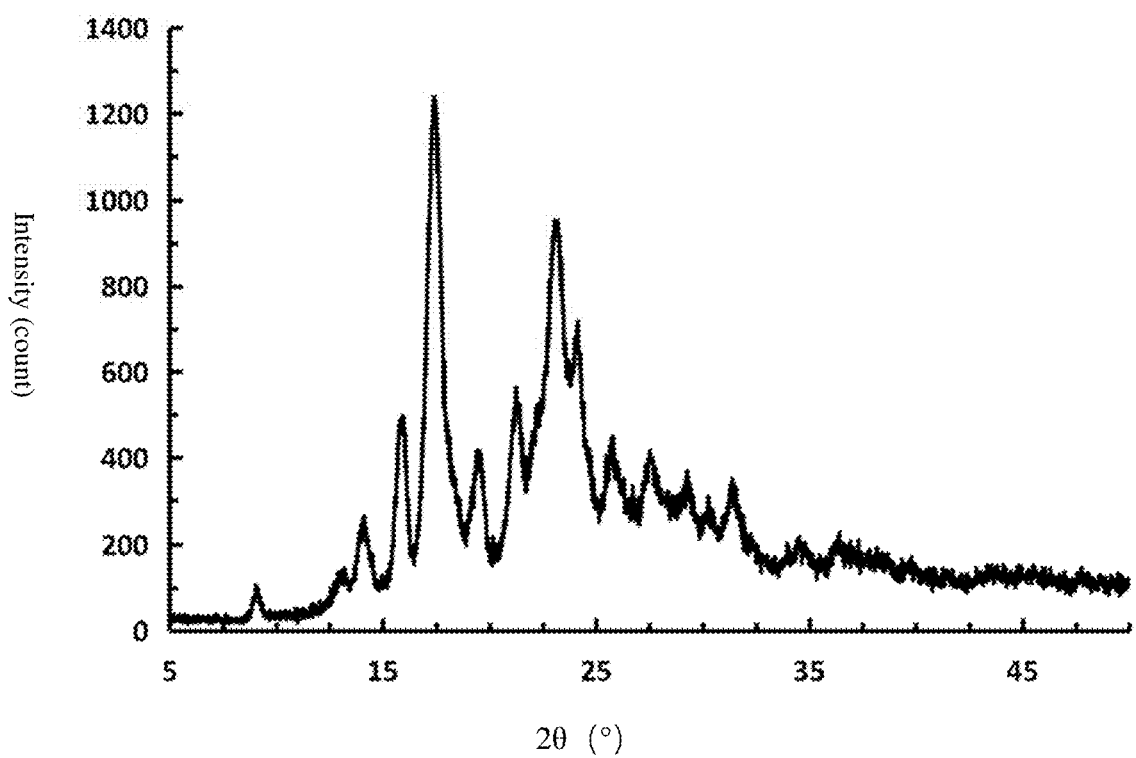
FIG. 16 is an XRPD pattern of the honokiol crystal form C treated at −80° C. in embodiment 14.
Figure 17:
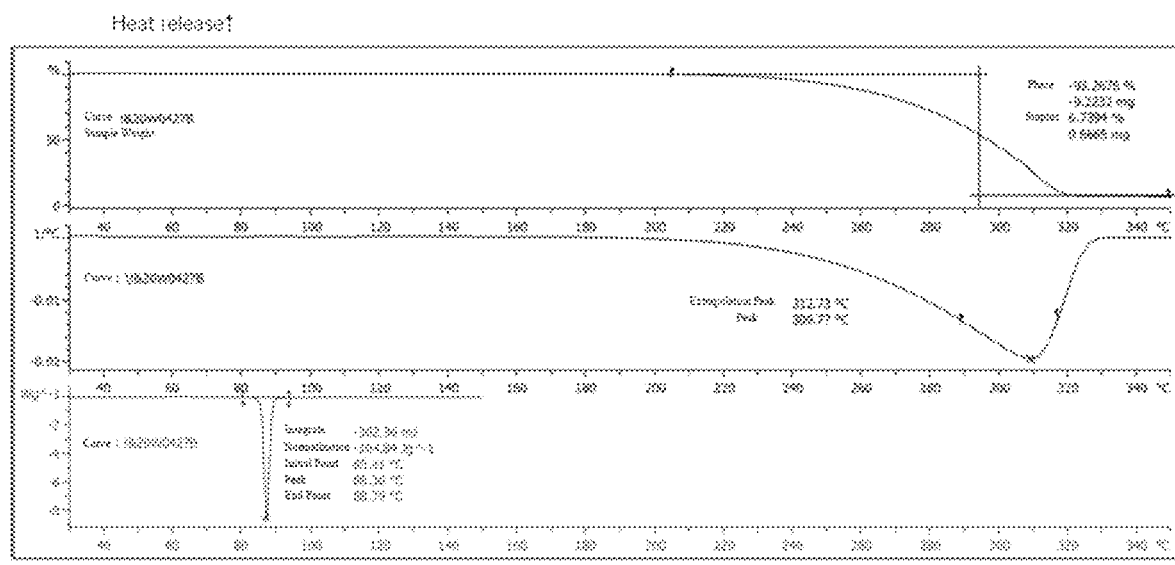
FIG. 17 is a TGA/DSC pattern of the honokiol crystal form C treated at −80° C. in embodiment 14.

Heating 1002.5 mg of honokiol crystal form A to the molten state at 85° C. in a crucible, then quickly placing the crucible in a refrigerator to maintain −80° C., standing overnight, and thus obtaining the solid as the honokiol crystal form C, of which the XRPD spectrum is shown in FIG. 16 and the TGA/DSC pattern is shown in FIG. 17.

The corresponding values of 2theta values and intensities of the honokiol crystal form C in the embodiment are shown in Table 7:

TABLE 7

Corresponding Values of 2theta Values and
Intensities of the Honokiol Crystal Form C

| No. | 2theta | Intensity % |
|---|---|---|
| 1 | 9.40 | 6.34 |
| 2 | 13.18 | 10.95 |
| 3 | 14.20 | 20.17 |
| 4 | 15.94 | 40.35 |
| 5 | 17.52 | 100 |
| 6 | 19.70 | 30.55 |
| 7 | 21.26 | 45.82 |
| 8 | 22.34 | 46.97 |
| 9 | 23.14 | 67.44 |
| 10 | 24.10 | 66.57 |
| 11 | 25.82 | 36.02 |
| 12 | 27.62 | 33.14 |
| 13 | 29.34 | 26.22 |
| 14 | 30.16 | 25.36 |
| 15 | 31.56 | 27.67 |
| 16 | 34.50 | 22.48 |

Embodiment 15: Preparation of the Honokiol Crystal Form C

Figure 18:
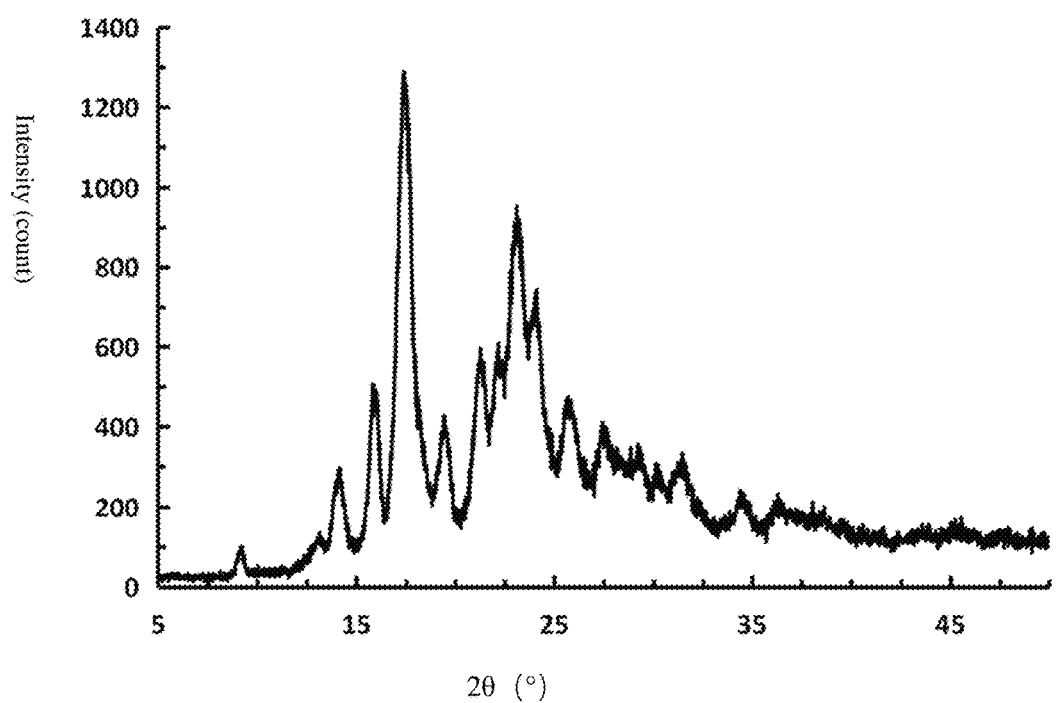
FIG. 18 is an XRPD pattern of the honokiol crystal form C treated at −196° C. in embodiment 15.

Heating 998.3 mg of honokiol crystal form A to the molten state at 85° C. in a crucible, then quickly placing the crucible in liquid nitrogen (−196° C.), standing overnight, and thus obtaining the solid as the honokiol crystal form C, of which the XRPD spectrum is shown in FIG. 18 and the TGA/DSC pattern is consistent with the TGA/DSC spectrum of the honokiol crystal form C prepared in embodiment 14.

The corresponding values of 2theta values and intensities of the honokiol crystal form C in the embodiment are shown in Table 8:

TABLE 8

Corresponding Values of 2theta Values and
Intensities of the Honokiol Crystal Form C

| No. | 2theta | Intensity % |
|---|---|---|
| 1 | 9.20 | 7.76 |
| 2 | 13.14 | 10.56 |
| 3 | 14.18 | 22.98 |
| 4 | 15.88 | 39.13 |
| 5 | 17.42 | 100 |
| 6 | 19.48 | 32.76 |
| 7 | 21.28 | 46.12 |
| 8 | 22.18 | 47.20 |
| 9 | 23.10 | 74.07 |
| 10 | 24.10 | 57.76 |
| 11 | 25.70 | 36.80 |
| 12 | 27.62 | 30.90 |
| 13 | 29.28 | 26.86 |
| 14 | 30.18 | 23.60 |
| 15 | 31.44 | 24.53 |
| 16 | 34.54 | 18.17 |

Embodiment 16: Preparation of Honokiol Amorphous Form

Figure 19:
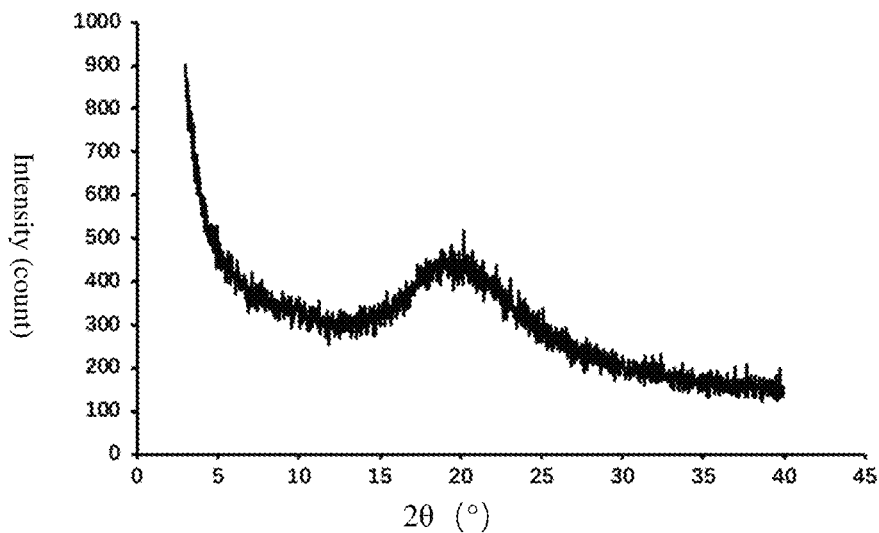
FIG. 19 is an XRPD pattern of the honokiol amorphous form prepared in embodiment 16.

Weighing about 15 mg of honokiol crystal form A into a 20 mL vial, dissolving in 0.5-1.0 mL of solvent DMSO, adding the antisolvent $H_2O$ under magnetic stirring, and stirring while adding dropwise. Centrifuging, discarding the supernatant, standing at room temperature, and thus obtaining an oily matter as the amorphous, of which the XRPD pattern is shown in FIG. 19.

Embodiment 17: TGA/DSC Tests for Honokiol Crystal Forms A, B and C

Thermogravimetric analysis (TGA): Instrument Manufacturer: METTLER-TOLEDO; Instrument Model: TGA/DSC2/1600; Test Conditions: taking an appropriate amount of trial-production sample under nitrogen atmosphere at 30-350° C., raising the temperature at a constant speed of 10° C./min, measuring changes in weight of the substance with the temperature, and plotting the weight-temperature change curve—TGA curve;
 differential Scanning calorimeter (DSC): Instrument Manufacturer: METTLER-TOLEDO; Instrument Model: DSC3+/500; Test Conditions: taking an appropriate amount of trial-production sample under nitrogen atmosphere at 30-150° C., raising the temperature at a constant speed of 10° C./min, and determining the DSC curve of the sample;
 heating the honokiol crystal forms A, B and C from room temperature to 150° C. respectively.

TGA results of the honokiol crystal form A show a 1.0% weight loss, and DSC results show two endothermic signals at 78.1° C. and 86.1° C. (peak temperature) as shown in FIG. 2.

TGA results of the honokiol crystal form B show a 1.3% weight loss, and DSC results show an endothermic signal at 86.1° C. (peak temperature) as shown in FIG. 11.

TGA results of the honokiol crystal form C show a 93.3% weight loss, and DSC results show an endothermic signal at 86.3° C. (peak temperature) as shown in FIG. 17.

Embodiment 18: Solubility Tests for Honokiol Crystal Forms A, B and C

Since the solubility of the drug directly affects the dissolution and oral bioavailability of the drug preparation, the inventor investigated the solubility of the honokiol crystal forms A, B and C in PBS. Preparing respective saturated solutions of the honokiol crystal forms A, B and C, shaking at 37°C for 4 h, and centrifuging and transferring the supernatant into a high performance liquid chromatograph. At the same time, preparing a standard solution of the honokiol (source: China Institutes for Food and Drug Control, Batch No.: 110730-201915, ID: EH2H-BMTW), and using the external standard method for quantification. Thus measured solubility of the honokiol crystal form A is 41.35 μg/ml, the solubility of the honokiol crystal form B is 43.66 μg/ml, and the solubility of the honokiol crystal form C is 48.12 μg/ml.

Embodiment 19: Photostability Tests for Honokiol Crystal Forms A, B and C

Figure 20:
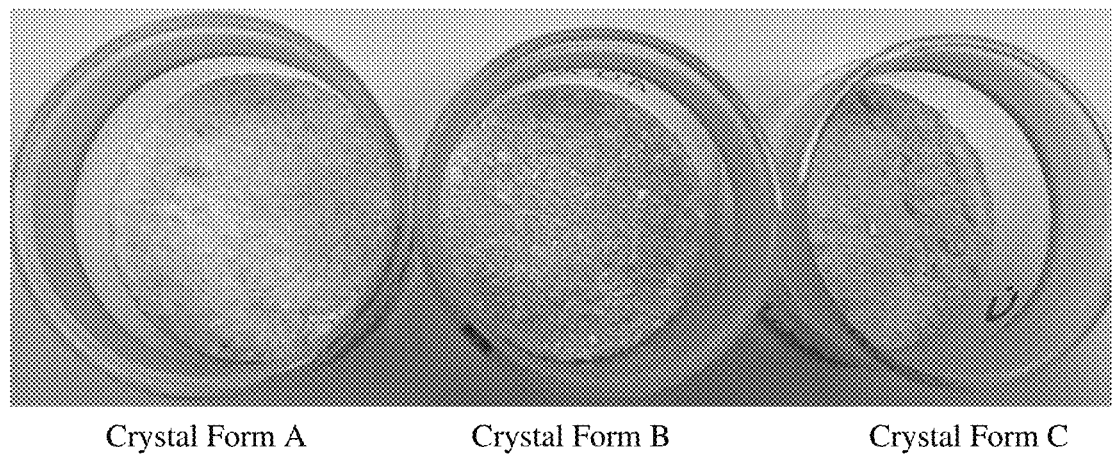
FIG. 20 is photographs of the honokiol crystal forms A, B and C after exposure to sunlight.

Standing the honokiol crystal forms A, B and C respectively in a small beaker in sunlight, and investigating the stability of each of the honokiol crystal forms A, B and C. Photographs of the honokiol crystal forms A, B and C after exposure to sunlight are shown in FIG. 20.

Embodiment 20: Stress Tests for Honokiol Crystal Forms A, B and C

Treating the honokiol crystal forms A, B and C under high temperature (60° C.), high humidity (relative humidity 92.5%, 25° C.) and high-light irradiation (illuminance 4500lx+500lx), respectively, diluting with methanol, and investigating the changes of related substances through testing with HPLC.

Figure 21:
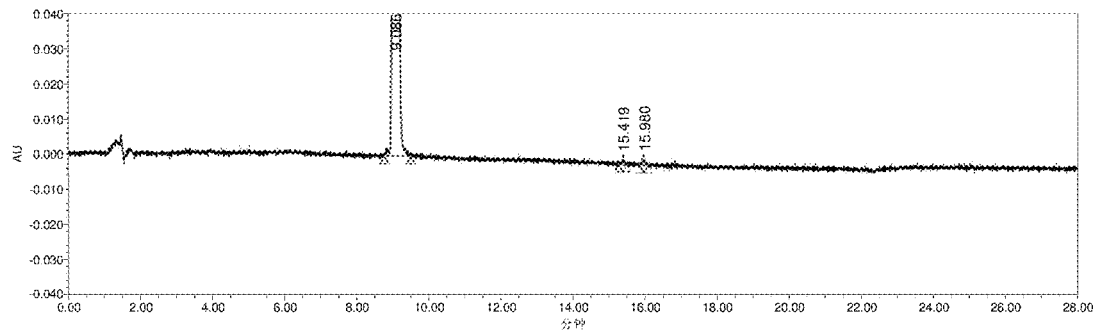
FIG. 21 is an HPLC of the honokiol crystal form A prior to a stress test.
Figure 22:
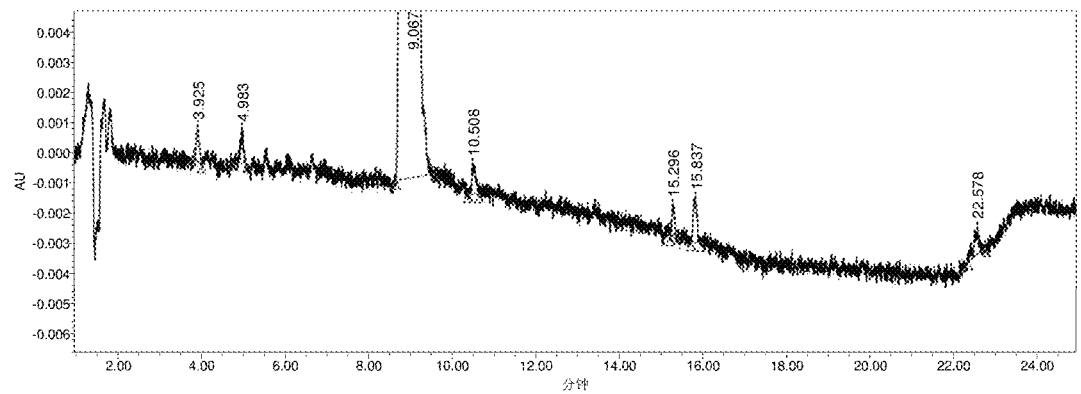
FIG. 22 is an HPLC of the honokiol crystal form A after a high temperature test.
Figure 23:
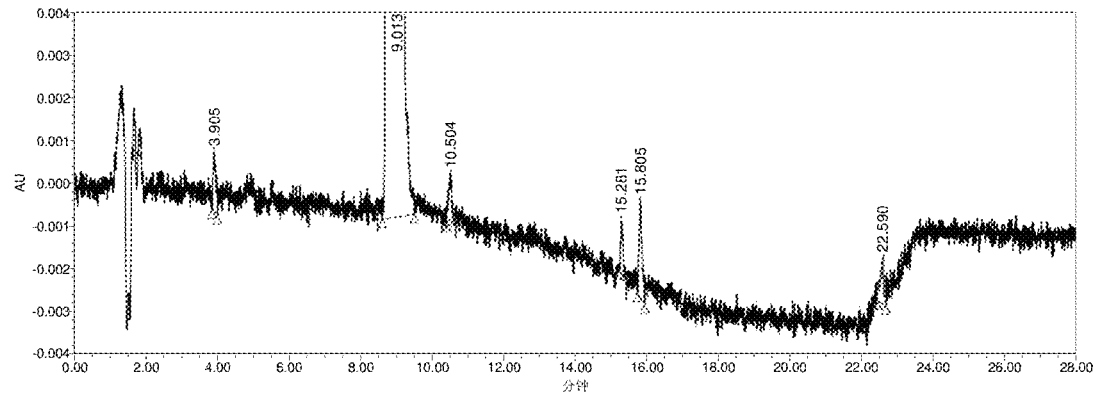
FIG. 23 is an HPLC of the honokiol crystal form A after a high humidity test.
Figure 24:
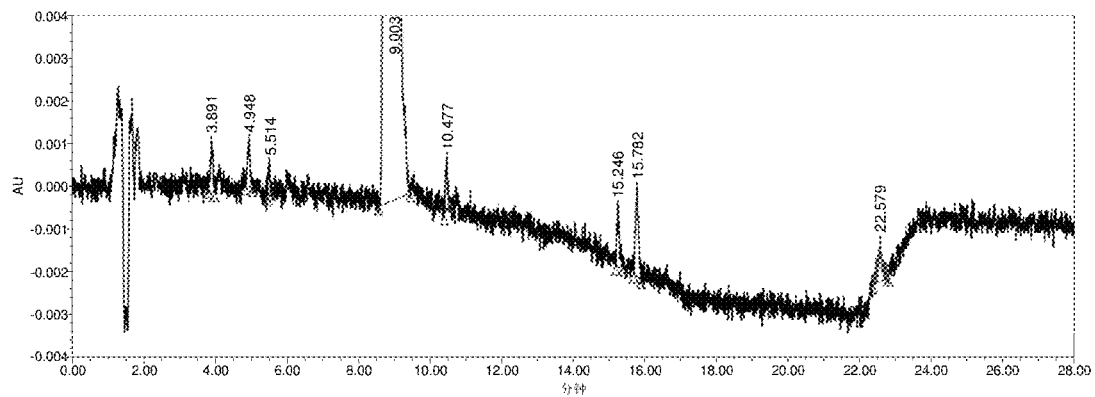
FIG. 24 is an HPLC of the honokiol crystal form A after a high-light irradiation test.

The purity of the honokiol crystal form A is 99.83% before the stress test, 99.63% after the high temperature test, 99.67% after the high humidity test, and 99.64% after intense light irradiation test respectively. The HPLCs of the honokiol crystal form A before the stress test is shown in FIG. 21, after the high temperature test is shown in FIG. 22, after the high humidity test in FIG. 23, and after the high-light irradiation test in FIG. 24 respectively.

Figure 25:
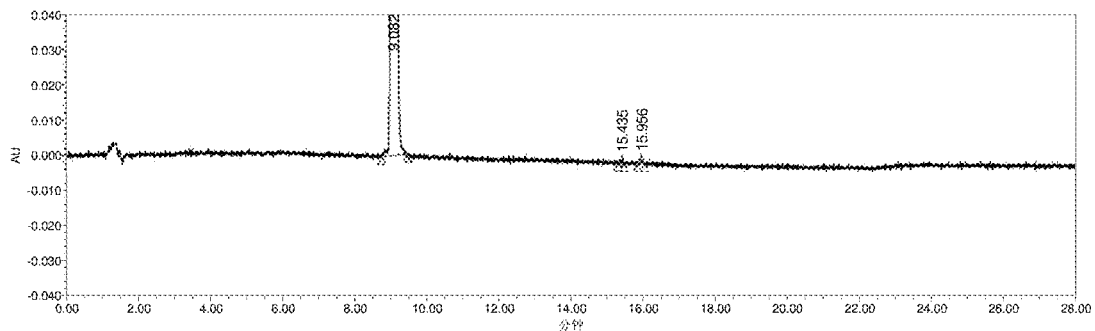
FIG. 25 is an HPLC of the honokiol crystal form B prior to a stress test.
Figure 26:
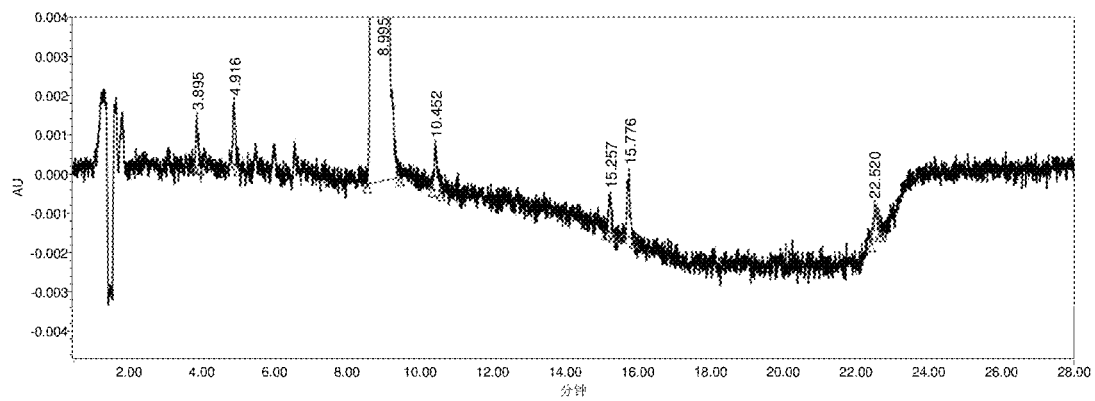
FIG. 26 is an HPLC plot of the honokiol crystal form B after a high temperature test.
Figure 27:
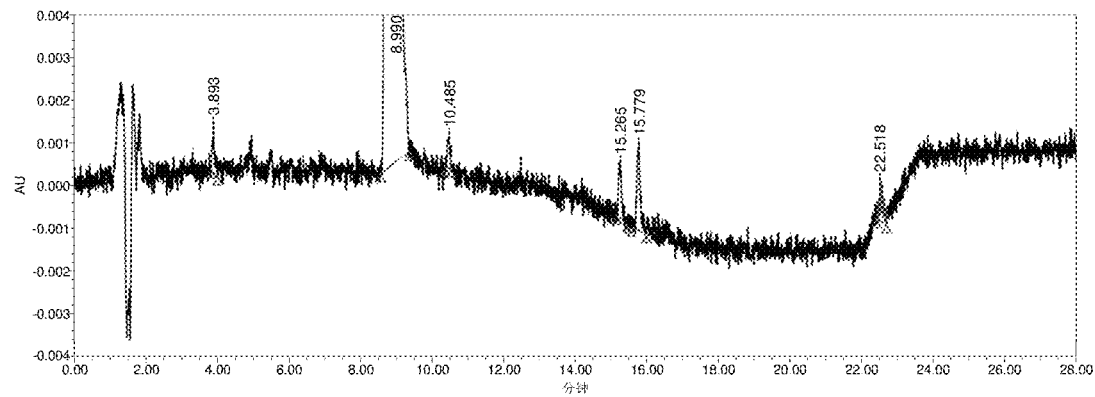
FIG. 27 is an HPLC of the honokiol crystal form B after a humidity test.
Figure 28:
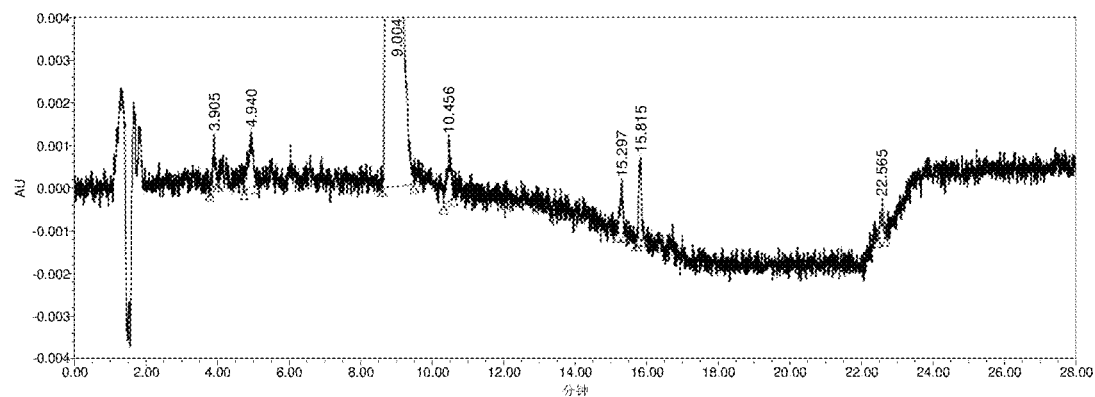
FIG. 28 is an HPLC of the honokiol crystal form B after a high-light irradiation test.

The purity of the honokiol crystal form B is 99.88% before the stress test, 99.70% after the high temperature test, 99.70% after the high humidity test, and 99.60% after the high-light irradiation test respectively. The HPLCs of the honokiol crystal form B before the stress test is shown in FIG. 25, after the high temperature test is shown in FIG. 26, after the high humidity test in FIG. 27, and after the high-light irradiation test in FIG. 28 respectively.

Figure 29:
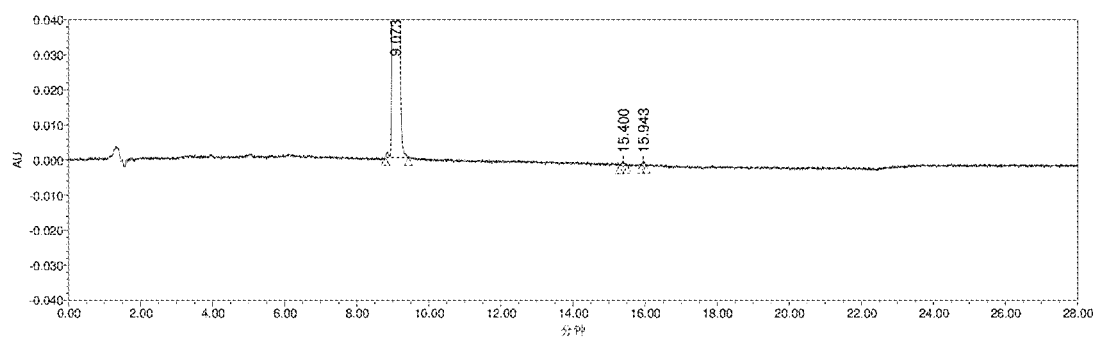
FIG. 29 is an HPLC of the honokiol crystal form C prior to a stress test.
Figure 30:
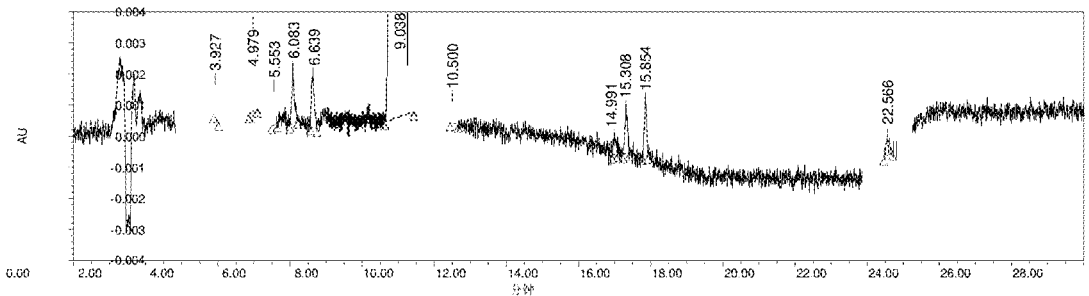
FIG. 30 is an HPLC of the honokiol crystal form C after a high temperature test.
Figure 31:
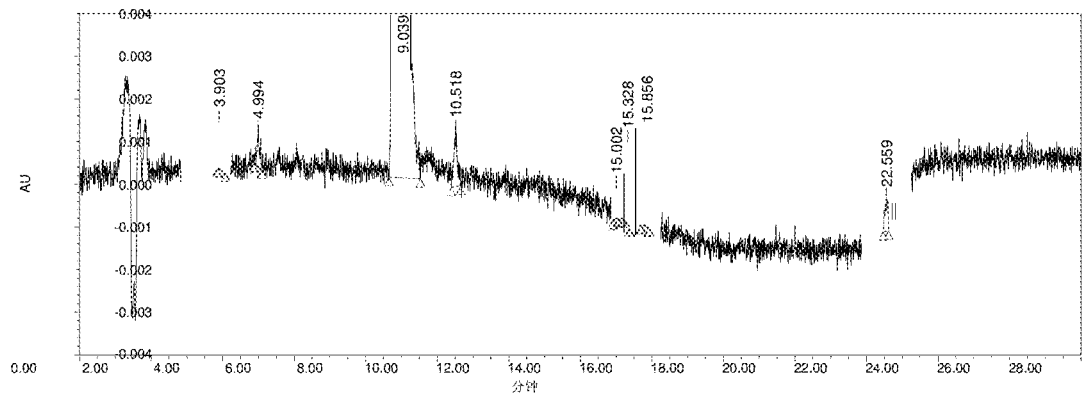
FIG. 31 is an HPLC of the honokiol crystal form C after a humidity test.
Figure 32:
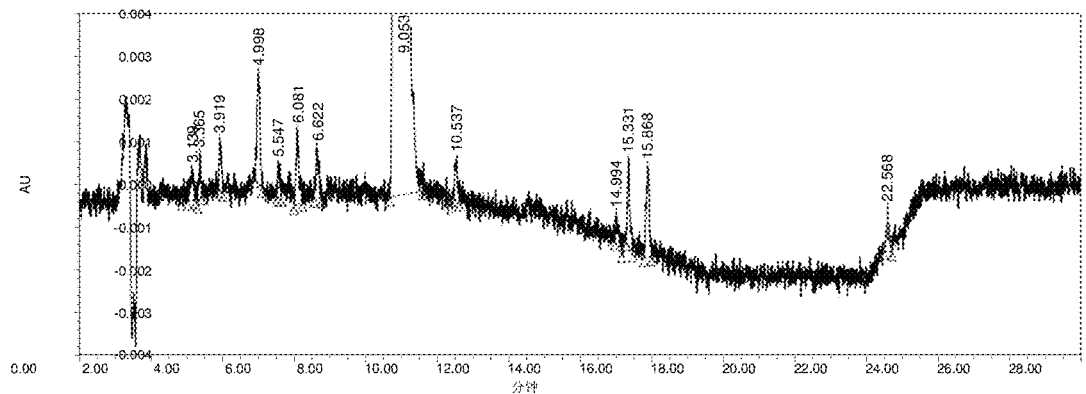
FIG. 32 is an HPLC of the honokiol crystal form C after a high-light irradiation test.

The purity of the honokiol crystal form C is 99.86% before the stress test, 99.36% after the high temperature test, 99.59% after the high humidity test, and 99.31% after intense light irradiation test respectively. The HPLCs of the honokiol crystal form C before the stress test is shown in FIG. 29, after the high temperature test is shown in FIG. 30, after the high humidity test in FIG. 31, and after the high-light irradiation test in FIG. 32 respectively.

Embodiment 21: Preparation of Honokiol Nano-Liposome Lyophilized Powder

All of the honokiol crystal forms A, B and C and the amorphous form are used to prepare the honokiol nano-liposome lyophilized powder with the same preparation method. Taking the honokiol crystal form B as an example, the preparation method is given below:

Dissolving 50 mg of honokiol crystal form B, 500 mg of soybean phospholipid, 200 mg of cholesterol and 200 mg of Cultured phosphatidylethanolamine in 50 mL of absolute ethanol, dissolving completely, injecting the solution into 300 mL of purified water, stirring for rotary evaporation to remove the ethanol, adding 800 mg of sucrose as the lyophilized excipient, and thus obtaining the honokiol nano-liposome lyophilized powder by freeze-drying. After reconstitution of the lyophilized powder, the particle size of honokiol nano-liposome is 114 nm as determined by a laser particle analyzer.

The invention claimed is:

1. A honokiol crystal form A, wherein a X-ray powder diffraction pattern of the honokiol crystal form A comprises characteristic peaks at 2theta values of 6.79°±0.2°, 9.10°±0.2°, 13.97°±0.2°, 14.97°±0.2° and 17.54°±0.2° under Cu-Kα radiation.

2. The honokiol crystal form A of claim 1, wherein the X-ray powder diffraction pattern of the honokiol crystal form A further comprises characteristic peaks at 2theta values of 20.61°±0.2°, 22.08°±0.2°, 24.01°±0.2° under Cu-Kα radiation.

3. A method for preparing the honokiol crystal form A of claim 1, comprising any one method selected from method I to method VIII:
 method I:
  dissolving honokiol in an organic solvent at 78° C. to 85° C. to obtain a honokiol solution, rapidly pouring the honokiol solution into another container, standing at room temperature overnight, centrifuging to collect solids to obtain the honokiol crystal form A, wherein the organic solvent is n-heptane, petroleum ether, cyclohexane, n-hexane, toluene, DCM, DMSO, NMP, chloroform, methanol/water, or ethanol/water;

method II:

placing honokiol in a container, then adding an organic solvent to another container, placing the opened container containing the honokiol in the container containing the organic solvent, sealing and standing at room temperature, centrifuging to collect solids to obtain the honokiol crystal form A, wherein the organic solvent is ethyl acetate, isopropyl acetate, tert-butyl methyl ether, chloroform, N-methylpyrrolidone, ethanol or acetonitrile;

method III:

placing honokiol in a container, dissolving in a solvent and filtering to obtain a clear honokiol solution, adding an antisolvent to another container, placing the opened container containing the clear honokiol solution in the container containing the antisolvent, sealing and standing at room temperature, centrifuging to collect solids to obtain the honokiol crystal form A, wherein the solvent is ethanol, tetrahydrofuran, chloroform, ethyl acetate or isopropanol, and the antisolvent is n-hexane or water;

method IV:

placing honokiol in a container, adding an organic solvent to obtain a suspension, magnetically stir the obtained suspension at room temperature, centrifuging to collect solids to obtain the honokiol crystal form A, wherein the organic solvent is methanol/water, acetonitrile/water, acetone/water, or dichloromethane/n-hexane;

method V:

placing honokiol in a container, adding an organic solvent to obtain a suspension, magnetically stir the obtained suspension at 40-60° C., centrifuging to collect solids to obtain the honokiol crystal form A, wherein the organic solvent is n-heptane, Tween/n-heptane, chloroform/n-heptane, or isopropanol/water;

method VI:

placing honokiol in a container, adding an organic solvent to obtain a suspension, magnetically stir the obtained suspension at a temperature cycling, centrifuging to collect solids to obtain the honokiol crystal form A, wherein the temperature cycling includes 2 cycles of 60° C.→5° C., 0.1° C./min, and 5° C.→60° C., 1.5° C./min, and wherein the organic solvent is n-heptane, ethanol/water, acetone/water, tetrahydrofuran/water, acetonitrile/water, ethyl acetate/n-heptane, tert-butyl methyl ether/n-hexane, or methyl isobutyl ketone/n-hexane;

method VII:

placing honokiol in a container, dissolving in an organic solvent, filtering and taking the filtrate, sealing the container containing the filtrate with a sealing membrane, making small holes on the sealing membrane, standing at room temperature to slowly volatilize, centrifuging to collect solids to obtain the honokiol crystal form A, wherein the organic solvent is chloroform, dichloromethane, methanol, isopropanol, or methyl isobutyl ketone;

method VIII:

placing honokiol in a container, dissolving in a solvent, adding an antisolvent under magnetic stirring while adding dropwise, standing, centrifuging to collect solids to obtain the honokiol crystal form A, wherein the solvent is ethanol, acetone, methyl isobutyl ketone, ethyl acetate, tert-butyl methyl ether, acetonitrile, dichloromethane or chloroform, and the antisolvent is n-heptane or water.

4. A honokiol crystal form B, wherein a X-ray powder diffraction pattern of the honokiol crystal form B comprises characteristic peaks at 2theta values of 6.15°±0.2°, 6.76°±0.2°, 8.96°±0.2° and 15.90°±0.2° under Cu-Kα radiation.

5. The honokiol crystal form B of claim 4, wherein the X-ray powder diffraction pattern of the honokiol crystal form B further comprises characteristic peaks at 2theta values of 17.49°±0.2° and 18.55°±0.2° under Cu-Kα radiation.

6. A method for preparing the honokiol crystal form B of claim 4, comprising:

heating a honokiol crystal form A to 80-82° C. and then cooling to the room temperature, and thus obtaining solid as the honokiol crystal form B.

7. A honokiol crystal form C, wherein a X-ray powder diffraction pattern of the honokiol crystal form C comprises characteristic peaks at 2theta values of 14.04°±0.2°, 15.84°±0.2°, 17.42°±0.2° and 19.48°±0.2° under Cu-Kα radiation.

8. The honokiol crystal form C of claim 7, wherein the X-ray powder diffraction pattern of the honokiol crystal form C further comprises characteristic peaks at 2theta values of 21.26°±0.2°, 23.10°±0.2° and 24.06°±0.2° under Cu-Kα radiation.

9. A preparation-method for preparing the honokiol crystal form C of claim 7, comprising:

(1) heating honokiol crystal form A to a molten state at 83-100° C. and stirring; and (2) placing the melt obtained in Step (1) rapidly at a quenching temperature of −20 to −196° C. to obtain a crystal, and separating the crystal as the honokiol crystal form C.

10. The method of claim 9, wherein the quenching temperature of Step (2) is −80 to −196° C.

11. An honokiol amorphous form, wherein the honokiol amorphous form has an X-ray powder diffraction pattern as shown in FIG. 19.

12. A method for preparing the honokiol amorphous form of claim 11, comprising:

(1) dissolving honokiol crystal form A in DMSO to obtain a solution;

(2) adding antisolvent water to the solution obtained in Step (1) and stirring; and (3) centrifuging, discarding supernatant, standing at room temperature, and thus obtaining an oily matter as the honokiol amorphous form.

13. A drug composition or drug product, comprising the honokiol crystal form A of claim 1, and pharmaceutical excipients.

14. A honokiol nano-liposome lyophilized powder, comprising the honokiol crystal form A of claim 1.

15. A method for preparing the honokiol nano-liposome lyophilized powder of claim 14, comprising:

dissolving the honokiol crystal form A, phospholipid, phosphatidylethanolamine and cholesterol in absolute ethanol to obtain a solution, injecting the solution that is completely dissolved into purified water, stirring for rotary evaporation to remove the ethanol, adding a lyophilized excipient, and freeze-drying to obtain the honokiol nano-liposome lyophilized powder.

16. A drug composition or drug product, comprising the honokiol crystal form B of claim 4 and pharmaceutical excipients.

17. A drug composition or drug product, comprising the honokiol crystal form C of claim 7 and pharmaceutical excipients.

18. A drug composition or drug product, comprising the honokiol amorphous form of claim 11, and pharmaceutical excipients.

19. A honokiol nano-liposome lyophilized powder, comprising the honokiol crystal form B of claim 4.

20. A honokiol nano-liposome lyophilized powder, comprising the honokiol crystal form C of claim 7.

21. A honokiol nano-liposome lyophilized powder, comprising the honokiol amorphous form of claim 11.

22. A method for preparing the honokiol nano-liposome lyophilized powder of claim 19, comprising:
dissolving the honokiol crystal form B, phospholipid, phosphatidylethanolamine and cholesterol in absolute ethanol to obtain a solution, injecting the solution that is completely dissolved into purified water, stirring for rotary evaporation to remove the ethanol, adding a lyophilized excipient, and freeze-drying to obtain the honokiol nano-liposome lyophilized powder.

23. A method for preparing the honokiol nano-liposome lyophilized powder of claim 20, comprising:
dissolving the honokiol crystal form C, phospholipid, phosphatidylethanolamine and cholesterol in absolute ethanol to obtain a solution, injecting the solution that is completely dissolved into purified water, stirring for rotary evaporation to remove the ethanol, adding a lyophilized excipient, and freeze-drying to obtain the honokiol nano-liposome lyophilized powder.

24. A method for preparing the honokiol nano-liposome lyophilized powder of claim 21, comprising:
dissolving the honokiol amorphous form, phospholipid, phosphatidylethanolamine and cholesterol in absolute ethanol to obtain a solution, injecting the solution that is completely dissolved into purified water, stirring for rotary evaporation to remove the ethanol, adding a lyophilized excipient, and freeze-drying to obtain the honokiol nano-liposome lyophilized powder.

* * * * *